(12) United States Patent
Bahatt et al.

(10) Patent No.: US 6,600,563 B1
(45) Date of Patent: Jul. 29, 2003

(54) OPTICAL RESONANCE ANALYSIS SYSTEM

(75) Inventors: Dar Bahatt, Foster City, CA (US); Jerry E. Cahill, Trumble, CT (US); Koichi Nishikida, Newtown, CT (US); Enrico G. Picozza, Hopkinton, MA (US); Paul G. Saviano, Norwalk, CT (US); David H. Tracy, Norwalk, CT (US); Yongdong Wang, Wilton, CT (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/486,424

(22) PCT Filed: Dec. 14, 1998

(86) PCT No.: PCT/US98/26543

§ 371 (c)(1),
(2), (4) Date: Jul. 17, 2000

(87) PCT Pub. No.: WO99/30135

PCT Pub. Date: Jun. 17, 1999

Related U.S. Application Data

(60) Provisional application No. 60/069,356, filed on Dec. 12, 1997.

(51) Int. Cl.$^7$ .......................... G01N 21/55; G01N 21/47
(52) U.S. Cl. ....................................... 356/445; 356/446
(58) Field of Search .......................... 356/445; 436/525

(56) References Cited

U.S. PATENT DOCUMENTS

| | | |
|---|---|---|
| 3,757,042 A | 9/1973 | Funk ............................ 348/81 |
| 3,888,283 A | 6/1975 | Cauffiel ....................... 138/150 |
| 4,882,288 A | 11/1989 | North et al. ................. 436/525 |
| 4,931,384 A | 6/1990 | Layton et al. .................. 435/7 |
| 4,992,385 A | 2/1991 | Godfrey ....................... 436/525 |
| 5,031,080 A | 7/1991 | Aikens et al. ................. 362/62 |
| 5,118,608 A | 6/1992 | Layton et al. ................ 435/7.1 |
| 5,327,225 A | 7/1994 | Bender et al. ............... 356/445 |
| 5,633,724 A | 5/1997 | King et al. .................. 356/445 |
| 5,822,073 A | 10/1998 | Yee et al. .................... 356/445 |
| 5,917,607 A | 6/1999 | Naya ........................... 356/445 |
| 5,991,048 A | * 11/1999 | Karlson et al. ............. 356/445 |

FOREIGN PATENT DOCUMENTS

| | | |
|---|---|---|
| EP | 0 286 195 A2 | 10/1988 |
| EP | 0 575 132 A1 | 12/1993 |
| WO | WO 97/22754 | 8/1995 |
| WO | WO 97/15819 | 5/1997 |
| WO | WO 97/32212 | 9/1997 |

OTHER PUBLICATIONS

"Applications of Charge Transfer Devices in Spectroscopy", Epperson et al., Analytical Chemistry, vol. 60, No. 5, Mar. 1, 1988, pp. 327,336.
"Victor Diffraction Of A Grating With Conformal Thin Films", W. A. Challener, J. Optical Society of America, vol. 13, No. 9, Sep. 1996.
"Real–Time Biospecific Interaction Analysis Using Surface Plasmon Resonance And A Sensor Chip Technology", Bio-Techniques, vol. 11, No. 5, 1991.

* cited by examiner

Primary Examiner—Georgia Epps
Assistant Examiner—M. Abutayeh

(57) ABSTRACT

An optical resonance analysis system comprising a sensor means (60) and an illumination means (400) for generating non-monochromatic illumination. The illumination means (400) further comprises a means for generating illumination at a plurality of angles, a lens system for projecting said illumination at said plurality of angles (390) and a dispersive device (380) for dispersing said illumination at each of said plurality of angles so that there is a correlation between said plurality of angles and the wavelengths of said illumination such that a resonance condition is generated on said sensor mean (60) for all wavelengths generated by said non-monochromatic source simultaneously. The analysis system also comprises a detection means (90) for detecting the reflected or transmitted illumination. Another embodiment comprises an anamorphic imaging means (120).

65 Claims, 9 Drawing Sheets

OPTICAL RESONANCE ANALYSIS SYSTEM

This application claims the benefit of provisional application 60/069,356 filed Dec. 12, 1997.

FIELD OF THE INVENTION

This invention relates generally to optical resonance analysis systems, specifically to certain sensor design aspects and to analysis systems comprising illumination and detection systems that utilize those sensors for analysis

BACKGROUND OF THE INVENTION

Because of the recent surge in applications, sensor based instruments are becoming very popular. This growth in applications has been primarily spurred by the biotechnology and the pharmaceutical industries especially from the enormous influx of information from the Human Genome Program. This drove of information has resulted in a corresponding spawning of new industries. Some of the newest, rapidly growing industries are: proteomics, where proteins, function and genomics come together; and pharmacokinetics where researchers attempt to find products of combinatorial synthesis that have binding properties to unique sites such as receptors, that typically result in a biological altering event. Both technologies rely on assays to be robust and process thousands of samples/day. It is obvious that handling this amount of material at these speeds would benefit from automated processes and miniaturization. One very popular application such as monitoring DNA/DNA, DNA/RNA, RNA/RNA hybridization has always been important, but as genes are discovered and associated with disease states, genetic analysis in diagnostics requiring hybridization assays becomes a necessity. However, to obtain the information to determine the genetically relevant data, thousands of tests need to be run on one sample if conventional technologies are used. New developments in sensor technology can reduce this analysis time from weeks to hours.

Sensors can be described as being composed of two parts; the transducer and the active site. The transducer is defined as the part of the device that is capable of reporting change in its environment. Transducers can operate in several different modes but the most common are optical based devices. Examples of optical based transducers include surface plasmon resonance (SPR) devices and planar waveguide devices and grating coupled waveguide devices. These types of sensors are described in U.S. Pat. Nos. 4,882,288, 4931,384, 4,992,385, and 5,118,608 all incorporated by reference. The sensor may consist of a single analysis site, a one dimensional or linear array of analysis sites or a two dimensional array of analysis sites.

Surface Plasmon Resonance Devices

Surface plasmon, which exists at the boundary between metal and dielectric, represents a mode of surface charge vibrations. The surface charge vibration is the vibration of the electrons on the metal surface generated by exterior light, these electrons behaving like free electrons. The surface plasmon wave extends into space or dielectrics as an evanescent wave and travels along the surface. The plasmon field satisfies the Maxwell equations and boundary conditions for p-polarized radiation. This boundary condition requires that the dielectric constants of metal and dielectrics have opposite sign. Since the common dielectric compound has a positive dielectric constant, the plasmon exists in the frequency region of the metal where the dielectric constant is negative. This situation happens at a frequency of the exterior light and lower frequencies, in which the real part of the refractive index of the metal is equal to or smaller than its imaginary part. For instance, for metals such as Gold, Silver or Aluminum, this frequency, the plasmon frequency, is about 5, 4 or 15 eV, respectively, resulting in a plasmon wave being available in a frequency range covering WV, Visible and Infrared regions. In this frequency range, since the wave vector of the surface plasmon is larger than that of the exterior light, the exterior light cannot interact directly with surface plasmon.

Utilization of the surface plasmon becomes possible when the exterior light wave is coupled with the surface plasmon by means of a grating or prism. These optical components provide an additional wave vector component to the exterior light, enabling energy exchange between the exterior light and the surface plasmon. The plasmon on the metal grating can interact with the exterior light by picking up an additional transverse momentum defined by the period of the structure.

On the other hand (as in the back illuminated Kretchman design), attenuated total reflection in a high refractive index material such as a prism provides additional transverse momentum so that the exterior wave has a wave vector larger than the vacuum wave vector, and the wave vector in the prism is large enough to match to the plasmon wave vector.

The prism method has been frequently utilized to determine optical constants of metals, because the resonance condition changes by the change in the refractive index. As gratings play an important role in promoting the surface plasmon, this in turn means that the surface plasmon causes some anomalies to grating performance. Because of the phenomena, theory of surface plasmons was also developed by grating scientists.

The SPR type device basically measures refractive index changes in a thin 1 $\mu$m evanescent field zone at its surface. The active surface defines the application and the specificity of the transducer. Various types of surface modifications can be used, for example, polymer coated transducers can be used to measure volatile organic compounds, bound proteins can be used to look for trace amounts of pesticides or other interactive molecules, DNA can be used to look for the presence of complementary DNA or even compounds that bind unique DNA sites. Specific sensors can be obtained by generating arrays of specific DNA sequences that hybridize the sample DNA. This technique is commonly referred to as array hybridization.

This type of sensor can operate in a gas or a liquid environment, as long as its performance is not degraded. Temperature range is selected by the application and should be controlled to better than 0.1° C. for maximum sensitivity measurements.

Arrays have been built using fluorescence as the reporter but technologies such as SPR may be used resulting in reduced hardware cost, and greater generality. The use of SPR is especially appropriate in monitoring the binding of combinatorial products because these products will not all have labels or properties such as fluorescence that one could monitor. An extension of surface plasmon resonance is the ability to combine this technique with others such as mass spectrometry. An example would be if a signal is detected on the SPR sensors indicating binding, a second technique could be used to identify the bound material.

Basic Grating Coupled Surface Plasmon Resonance Physics and Behavior

Surface Plasmon Resonance

The propagation of electromagnetic wave is expressed in terms of the waves equation as $$E(x,t) = E_0 \exp i(K_x x - \omega t) \quad (1)$$

where $K_x$ and D represent the wave vector in the x-direction and the angular frequency of the wave, respectively. The terms, x and t are distance and time, respectively. The plasmon wave vector is given by $$K_x = 2\pi\nu[\epsilon_0+\epsilon_1]^{1/2} = (\omega/c)[\epsilon_0\epsilon_1/(\epsilon_0+\epsilon_1)]^{1/2} = (2\pi/\lambda)[\epsilon_0\epsilon_1/(\epsilon_0+\epsilon_1)]^{1/2}. \quad (2)$$

where $\epsilon_0$ and $\epsilon_1$ are dielectric constants of dielectric compound and metal and $\lambda$ is the wavelength of the exterior light. Twice the imaginary part of $K_x$, $2K_{xi}$, determines the distance the plasmon electric field decays to 1/e along the metal surface.

Gratings provide the standing wave vector parallel to the boundary depending on the groove space and order of the grating. Thus, resonance absorption occurs when the exterior light wave vector component in the boundary plus the grating vector equal to the plasmon vector as given by $$(\omega/c)\sin\theta + 2\pi m/a = (\omega/c)[\epsilon_0\epsilon_1/(\epsilon_0+\epsilon_1)]^{1/2} \quad (3)$$

where a and m are the groove spacing and the order of grating. Term $\theta$ is the incident angle of the exterior light.

Resonance Width

For a given metal/dielectric boundary, the SPR wavevector $K_x$ corresponding to a given frequency $\omega$ can be estimated as given in eq (1).

We define $k_{sp}$ as the real part of the center wavevector of the plasmon. The Lorentzian full width at half maximum, in the absence of radiative coupling, is given by twice the imaginary part of the wavevector, $k_i$.

$$\Delta k_{FWHM} = 2 k_i \quad (4)$$

The HWHM $\Delta k_{1/2}$ is obviously half of this value.:

$$\Delta k_{1/2} = k_i \quad (5)$$

Addition of radiative coupling or other losses can only increase the SPR linewidth. The question we seek to answer is the following: What is the non-radiative SPR width observed in terms of input wavelength $\lambda$ or angle $\theta$, for both the grating coupling and prism coupling (Otto or Kretchman) cases.

Basic SPR Coupling Equations
Grating Coupling $$k_{sp} = (2\pi/\lambda)\sin\theta + (2\pi m/a) \quad (6)$$

where $\lambda$ is the vacuum wavelength, $\theta$ is the input angle in air (not in the sample medium), m is the integer grating coupling order, and a is the grating groove pitch.

Prism Coupling:

$$k_{sp} = (2\pi n/\lambda)\sin\theta_P \quad (7)$$

where n is the refractive index of the coupling prism and $\theta_P$ is the input coupling angle within the prism medium.

In the case where the wavelength is fixed and the angle varies, since $\lambda$ is unchanged and monochromatic, the plasmon itself is unaffected by the angle change. Only the efficiency of in-coupling is affected. Imagine that the angle is initially set at $\theta$ such that the plasmon is maximally excited. Now we shift the input angle to $\theta'$ such that the excitation is reduced by 50%, to one of the half intensity points. Then we have simply $$d\theta_{1/2} = \theta' - \theta = \Delta k_{1/2}[\partial\theta/\partial k] \quad (8)$$

For the grating case, Eqn 6 gives $$\partial\theta/\partial k = \lambda/\{2\pi \cos\theta\} \quad (9)$$

so that the in-air half-angle is $$d\theta_{1/2} = \Delta k_{1/2}\lambda/(2\pi \cos\theta) \quad (10)$$

For the prism case, Eqn 7 gives $$\partial\theta_P/\partial k = \lambda/\{2\pi n \cos\theta_P\} \quad (11)$$

so that the in-prism half-angle is $$d\theta_{1/2\,(Prism)} = \Delta k_{1/2}\lambda/(2\pi n \cos\theta) \quad (12)$$

If the prism is beveled to allow near-normal incidence coupling from air into the prism, then according to Snell's law the differential angle in air is n times that inside the glass. The net result for the prism case is that the in-air half-angle is $$d\theta_{1/2\,(Air)} = \Delta k_{1/2}\lambda/(2\pi \cos\theta_P), \quad (13)$$

a result nearly identical to the grating result (10).

In other words, to the extent that the nominal incoupling angle in air for the grating case is similar to the incoupling angle in glass for the prism case, the in-air angular resonance widths are nearly the same. The full FWHM angular width in air, for either case, is found from doubling (10) or (13) to be $$\Delta\theta_{FWHM} = 2 k_i\lambda/(2\pi \cos\theta) \quad (14)$$

In the case where the angle is fixed and the wavelength varies, since $\omega$ varies when we change $\lambda$, the plasmon itself changes as we vat, the input wavelength. At the same time, the coupling conditions also change so the new plasmon is not being excited on-resonance. Both effects need to be taken properly into account.

Assume that we start, as before, with $\lambda$ and $\theta$ chosen so that we are tuned to the SPR peak initially, which has wavevector $k_{sp}$. Now we change the wavelength to $\lambda'$ so as to attempt to reach the half intensity point. That is, we seek to have $$\lambda' = \lambda + \Delta\lambda_{1/2} \quad (15)$$

As we do this, the plasmon wavevector must change to $k'_{sp}$ such that $$k'_{sp} 32 k_{sp} + (\partial k/\partial\lambda)(\lambda' - \lambda) \quad (16)$$

Here, the partial $\partial k/\partial\lambda$ is calculated numerically from (1) using tabulated dielectric constant data for the materials forming the SPR device. Note that in general, it is negative.

At the same time the wavevector $k_L$ being launched is given by Eqn (6) or (7), depending on what kind of coupler we are using.

For the grating case, we launch at wavevector $$k_L = (2\pi/\lambda')\sin\theta + (2\pi m/a) \quad (17)$$

-continued $$= k_{sp} + 2\pi\sin\theta[1/\lambda' - 1/\lambda]$$

$$\cong k_{sp} - 2\pi\sin\theta[(\lambda' - \lambda)/\lambda'],$$

whereas for the prism case $$k_L = (2\pi n/\lambda')\sin\theta = [\lambda/\lambda']k_{sp} = [\lambda/(\lambda + \Delta\lambda)]k_{sp} \qquad (18)$$

$$\cong [(\lambda - \Delta\lambda)/\lambda]k_{sp} = k_{sp} - [\Delta\lambda/\lambda]k_{sp}$$

To reach the half intensity point by tuning $\lambda$, we require that the mismatch between the launch wavevector $k_L$ and the modified plasmon wavevector $k_{sp}'$ be exactly $\Delta k_{1/2} = k_i$:

$$k_L - k_{sp} = \pm k_i \qquad (19)$$

Combining (16) and (17), Eqn 19 becomes, for the grating case, $$-2\pi\sin\theta[(\lambda'-\lambda)/\lambda^2] - (\partial k/\partial\lambda)(\lambda'-\lambda) = \pm k_i \qquad (19)$$

or $$\Delta\lambda_{1/2} \equiv \lambda' - \lambda = -\frac{\pm k_i}{2\pi\sin\theta/\lambda^2 + \partial k/\partial\lambda} \qquad (20)$$

For the prism case, Eqns (16) and (18) lead in a similar fashion to $$-k_{sp}[(\lambda'-\lambda)/\lambda - (\partial k/\partial\lambda)(\lambda'-\lambda) = \pm k_i$$

or $$\Delta\lambda_{1/2} \equiv \lambda' - \lambda = -\frac{\pm k_i}{k_{sp}/\lambda + \partial k/\partial\lambda} \qquad (21)$$

Note that the HWHM in $\lambda$ given by (20) and (21) for grating and prism coupling respectively give quite different results. In general, the width will be wider for prism coupling, since the two terms in the denominator have opposite signs, for example the first term is positive and the second term is negative, and similar magnitudes, tending to reduce the denominator and hence increase the quotient.

Note also that the FWHM resonance widths are double the HWHM values of (20) and (21):

$$\Delta\lambda_{FWHM} = 2 \Delta\lambda_{1/2}$$

Planar Waveguide Sensors

Waveguide sensors consist of one or more layers of dielectric materials coated with a thin film of material of higher index of refraction. The waveguide sensor responds to: changes in the refractive index $n_C$ of the cover medium C; adsorption of molecules out of a gaseous or liquid phase cover, to form a surface layer of thickness dr and refraction index $n_F$. and, if used as dispersing element (Propagation angle in the waveguide depends on the wavelength), it can record the absorption spectrum of molecules on the surface. The sensitivity can be expressed as the change in the effective index of refraction N (of a guided mode TE or TM) in cases 1–3. In the case of absorption measurements (and using the guide as a dispersive element) the sensitivity is determined by the minimum detectable absorption.

This type of sensor can operate in a gas or a liquid environment, as long as its performance is not degraded. Temperature range is selected by the application and should be controlled to better than 0.1° C. for maximum sensitivity measurements. Substrates include sapphire, ITO, fused silica, glass (Pyrex, Quartz,), plastic, Teflon, metal, and semiconductor materials (Silicon). Waveguide films include $SiO_2$, $SiO_2$—$TiO_2$, $TiO_2$, $Si_3N_4$, lithium niobate, lithium tantalate, tantalum pentoxide, niobium pentoxide, GaAs, GaAlAs, GaAsP, GaInAs, and polymers (polystyrene). Waveguide film thickness is usually in the range of 100–200 nm. Example ranges of indexes of refraction include from 1.4–2.1. Chemoselective coatings can be placed on the waveguide film surface. Light coupling into the waveguide can be achieved by using surface relief gratings or prisms.

A way to measure the changes in the effective index is by the change in the angle at which the mode exits from the waveguide. This can be done by an array detector, which at the same time can measure the intensity at each wavelength. In that case the time of measurement is typically 100–200 $\mu$sec.

Associated system components usually include gratings (to match the Dangle dispersion curve of the waveguide), mirrors, lenses, polarizers, white light sources, and array detectors.

Multiple assays and analytes are possible as long as the waveguide can be spotted with different chemistries, the incoming light is split into multiple collimated light beams, there is no mixing of the light beams inside the guide, and the detection can be done simultaneously for all assays/analytes.

Possible applications are analytical chemistry, humidity and gas sensing, PH measurement, bio- and immuno-sensor applications, molecular recognition in biology, signaling transduction between and within cells, affinity of biotinylated molecules (bovine serum albumin) to Avidin or strept-Avidin, antigen-antibody interactions (immunobinding of rabbit/goat anti-h-IgG antibody to the human immunoglobulin h-IgG antigen) etc. The grating coupled waveguide sensor can measure the number, size and shape of living cells growing on its surface, in real time and non-invasively. Applications include toxicology and cancer research, pharmacology—drug determination. A waveguide supported lipid bilayer is the closest to real cell membrane simulation, and can be used for drug screening as well as blood-brain barriers. Waveguides can be used to analyze properties of bilayer lipid membranes (BLM) and other thin films, to measure protein-BLM interaction, and the thickness, density, anisotropy, and the reaction of thin films to perturbations in time. Other applications include using long DNA molecules as a surface coat to measure hybridization and protein binding, molecular self-assembly, nanoscience, and analysis of association and dissociation kinetics.

Grating Coupled Waveguide Sensors

Grating couplers are used for efficient coupling of light into or out of a waveguide that consists of one or more layers of dielectric materials. At the same time they can be used for measuring the effective index of refraction N of all possible TE and TM modes. The primary sensor effect is a change $\Delta N$ in the effective refractive index N of the guided modes induced by the adsorption or binding of molecules from a sample on the waveguide surface. From $\Delta N$ it is possible to calculate the refractive index, thickness and surface coverage of the adsorbed or bound adlayers. Provided that thin monomode waveguide film F with a large difference $n_F - n_S$ between the refractive indexes of film F and substrate S are used, integrated optics guarantees high sensor sensitivities (sub-monomolecular adsorbed layer). ΔN is measured only in the grating region which is where the sample should be placed. With optimal grating design a coupling efficiency of the order of 45–90% can be achieved.

A grating coupler can operate in a gas or a liquid environment, as long as its perfomance is not degraded. Temperature range is selected by the application and should be controlled to better than 0.1° C. for maximum sensitivity measurements. Substrates include sapphire, ITO, fused silica, glass (Pyrex, Quartz,), plastic, teflon, metal, and semiconductor materials (Silicon). Waveguide films include $Sio_2$, $SiO_2$—$TiO_2$, $TiO_2$, $Si_3N_4$, lithium niobate, lithium tantalate, tantalum pentoxide, niobium pentoxide, GaAs, GaAIAs, GaAsP, GaInAs, and polymers (polystyrene). Waveguide film thickness can be in the range of 100–200 nm and indexes of refraction can be in the range of 1.4–2.1. Gratings can be made by embossing, ion-implantation and photoresist techniques, on the substrate or in the waveguide film. Typical numbers are 1200–2400 lines/mm, 2×16 mm in size and 1:1 aspect ratio (20 nm features). Chemoselective coatings can be placed on the waveguide film surface.

For incoupling gratings mechanical angle scanning measurement time is typically 2–3 sec. If an array of sources is used in conjunction with a lens this time is shortened. For an outcoupling grating and a position sensitive detector (no moving parts), it is typically 100–200 μsec.

Associated system components usually include optics, mirrors, lenses, polarizers, light sources, light source arrays, laser sources, single or position sensitive detectors, rotation stages, and stepper motors Multiple assays and analytes are possible as long as the waveguide can be spotted with different chemistries, the incoming light is split into multiple collimated light beams, there is no mixing of the light beams inside the guide, and the detection can be done simultaneously for all assays or analytes.

Applications include analytical chemistry, humidity and gas sensing, PH measurement, bio- and immuno-sensor applications, molecular recognition in biology, signaling transduction between and within cells, affinity of biotinylated molecules (bovine serum albumin) to Avidin or strept-Avidin), antigen-antibody interactions (immunobinding of rabbit/goat anti-h-IgG antibody to the human immunoglobulin h-IgG antigen) etc.

Analysis Systems

Analysis systems utilizing these types of optical resonance devices (SPR and waveguides) typically include an illumination system having the capability to project light at various frequencies or angles onto the resonance device and a detection system for detecting the corresponding resonance peaks.

The illumination systems are typically composed of a light source, a means for causing the light source to impinge on the sensor at different angles or at different frequencies, and optics to facilitate imaging the source onto the sensor. The choice of light source is based on the wavelength region required and the etendue (solid angle X photon flux) of the optical system. There are a large variety of broadband or monochromatic sources to choose from, such as: incandescent, LED's, super luminescent diodes, lasers (fixed and tunable, diode, solid state, gas), gas discharge lamps (line and continuum), with or without filters. Wavelength scanning is usually accomplished by coupling the source with filter wheels, scanning monochrometers or acousto-optical tunable filters, or in the case of a laser source by using a tunable diode laser. Angle scanning is usually accomplished by mechanically positioning the source at a series of angles with relationship to the sensor. In addition the source must be oriented and focused so that it optimally projects onto the sensor.

Light rays from the illumination system are reflected from the sensor with their angle of reflection equal to their angle of incidence. Thus the rays will typically span a small range of angles in the perpendicular plane. The detector is typically positioned to optimally receive the rays coming from the sensor. Other important detector considerations are resolution, pixel size, number of pixels, the algorithms that will be used for analyzing the resonance wavelengths or angles, and the chemistry occurring on the detector.

In resonance measurement, a peak or a dip is obtained over a sometime sloped baseline. When the measurement is performed on another sample at a different concentration, this peak or dip will shift depending on the change in refractive index corresponding to concentration difference between the two samples. The concentration can then be predicted using a calibration model relating the peak or dip shift to concentration.

SUMMARY OF THE INVENTION

This invention is directed toward an analysis system, comprising an illumination and detection system, which utilizes a surface plasmon device or a waveguide as a sensor.

The invention is further directed toward an illumination system utilizing an array of light sources to facilitate angle or wavelength scanning.

The invention is further directed toward a means for providing independent axial and rotational positioning of the array of light sources.

The invention is further directed toward utilizing a diffraction grating or a diffractive optical element as a pre-dispersive or post-dispersive element in the analysis system allowing the use of low cost, broad band light sources.

The invention is further directed toward an anamorphic optical design that allows the analysis system to generate and detect resonances, from a one dimensional array of sites on the same substrate, simultaneously.

The invention further comprises a method for predicting concentrations using a calibration model relating the resonance peak shift to concentration.

DETAILED DESCRIPTION OF THE INVENTION

Figure 1:
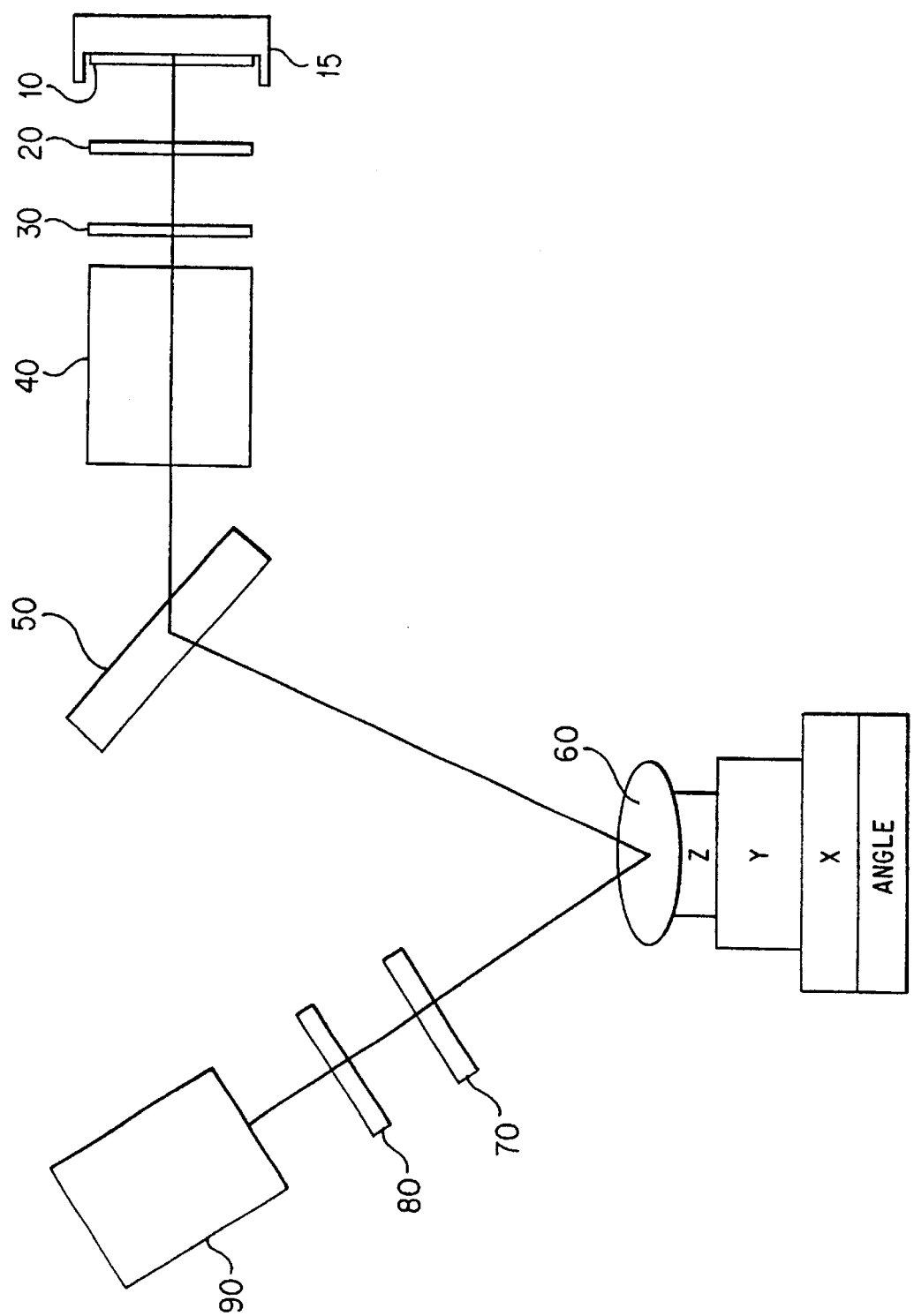
FIG. 1 shows an embodiment of the invention.

FIG. 1 shows an embodiment of the invention utilizing an angle scanning illumination system, a sensor with a two dimensional array of sites derivatised or sensitized with the same sample (for the analysis of multiple assays) or different samples (for the analysis of a single assay), and sequential detection. A light source 10 is mounted on a device 15 that allows independent axial and rotational movement. The light emitted from the source travels through a polarizer 20, a filter 30, a lens system 40, a pre-dispersive grating 50, and impinges on a sensor 60. Light reflected from the sensor 60 then travels through an imaging lens 70, an angle or wavelength stop 80 to a detector 90.

Illumination System

Source

Figure 3:
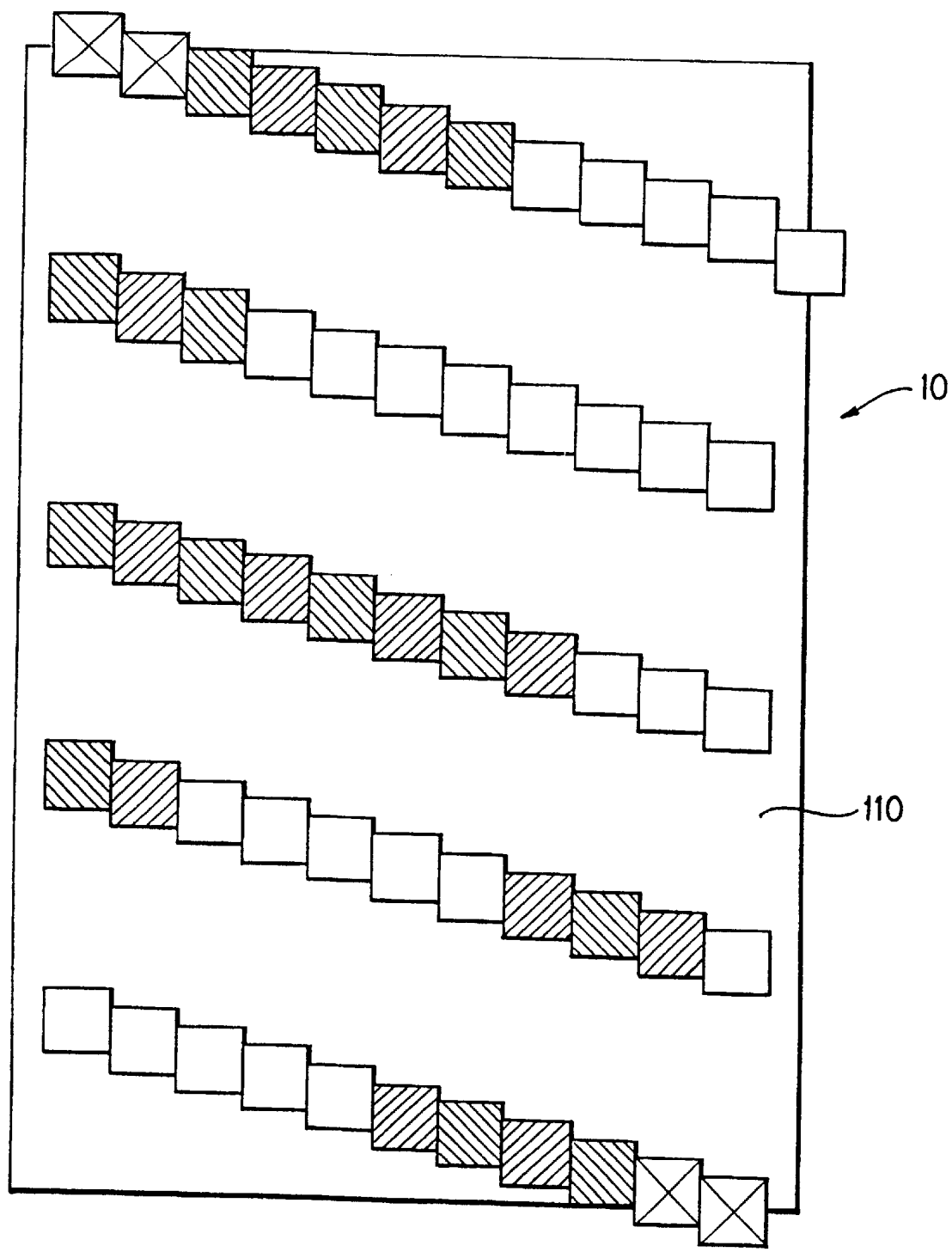
FIG. 3 shows an example of a two dimensional array of light sources.

The source is constructed as shown in FIG. 3, a two dimensional array of sources 110. The choice of light source is based on the wavelength region required and the etendue (solid angle X pupil area) of the optical system. In the case of SPR, the sensor resonance becomes sharper with increasing source wavelength. The advantage of having narrow resonance is in the ability to detect smaller shifts (sensitivity). On the other hand, the resonance decay length increases with wavelength and thus the reaction site dimensions have to increase (spatial resolution, and system throughput). There is a large variety of broadband or monochromatic sources to choose from, such as: incandescent, LED's, super luminescent diodes, lasers (fixed and tunable, diode, solid state, gas), Gas discharge lamps (line and continuum), with or without filters. Incoherent sources are preferred in order to eliminate speckle noise. An example of a light source in this embodiment is a Hewlett-Packard HSDL-4400 LED emitting at 875 nm, where the resonance width is 0.3 degrees or 5 nm. At this wavelength the SPR decay length is of the order of 25 microns. When an array of LED's is used, and placed at the focal plane of the angle-scanning lens system as shown in FIG. 1, 40 each LED corresponds to a different angle of illumination. A spacing of 0.395 mm between the LED's in the array corresponds to an angular resolution of 0.3 deg at f=75 mm, and 0.038 deg at f=600 mm. An array length of 35 mm corresponds to a total angle of 26 deg at f=75 mm, and 3.3 deg at f=600 mm. This range of angle step and angle range allows for both low resolution/large coverage and high resolution/small coverage scanning.

Mount for Independent Axial and Rotational Movement.

Figure 4:
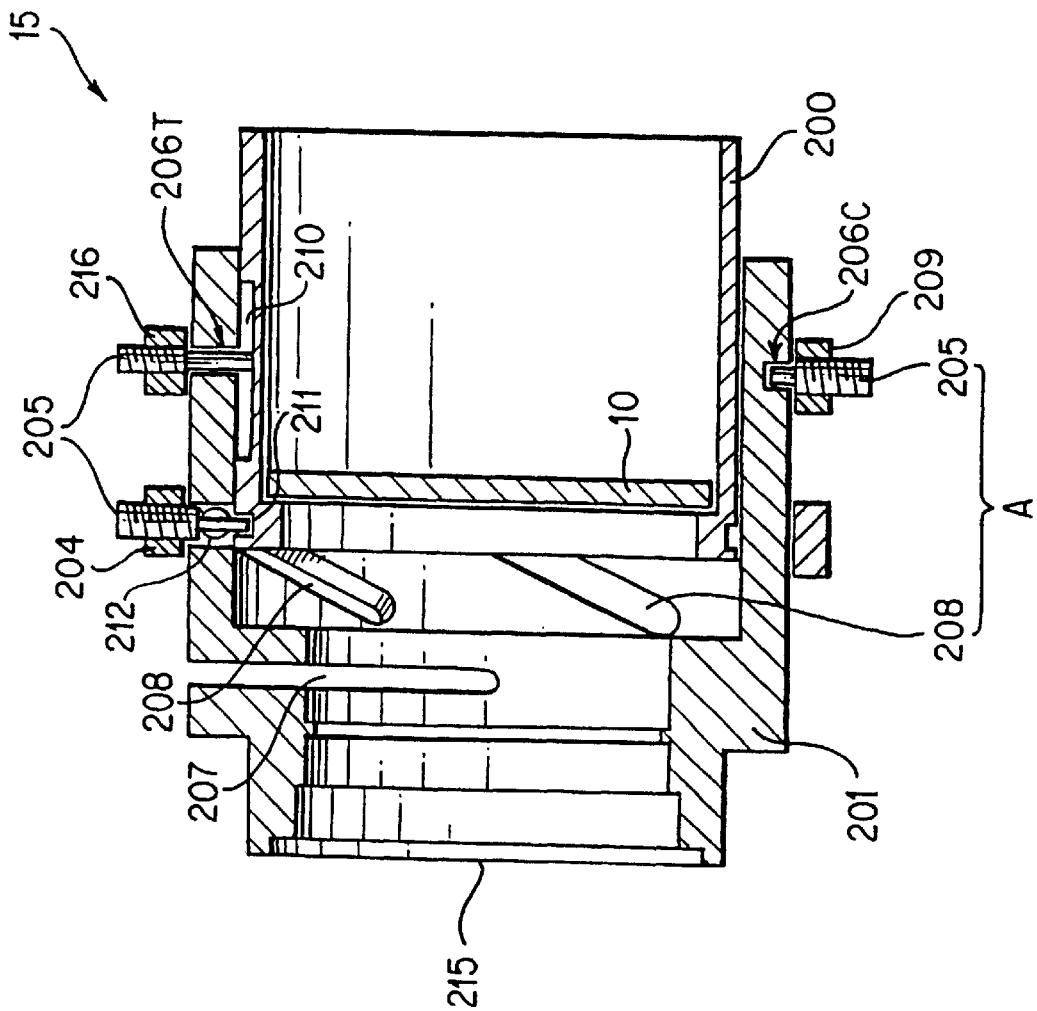
FIG. 4 shows a mechanism that allows independent axial and rotational movement of the source.

As shown in FIG. 1 the source 10 is mounted on a device 15 that allows independent axial, or focusing, and rotational movement. The design and arrangement of this device assembly as shown in FIG. 4 allows the source to move freely and independently in the specified motions of rotation and focus, over the desired ranges. Additionally, the assembly is designed to be compatible with standard bayonet photographic lens mounting configurations. The design of the focusing motion components was intended to take advantage of the increased sensitivity of axial motion inherent in the application of rotational movement within helical patterned grooves, and the smooth, gradual effect of an inclined plane this interaction produces.

In particular, the invention is directed to a method by which the helical slots 208 are formed in the stationary cylindrical housing 201. Recognizing the need for additional, specialized tooling, not necessarily found in model making shops, an alternate method was developed that utilizes standard, common milling machine tooling and professional skills. Introducing a true helical slot or groove into a cylindrical surface requires a multi-axis lathe with sophisticated electronic control. Manual methods of control in a lathe or milling machine are possible but very tedious and do not produce a smooth surface to the sides of the slot or groove. In this case, the lack of tooling accessories and a desire to produce helical slots quickly and with simplicity, inspired the following pseudo-helical fabrication method.

Figure 5A:
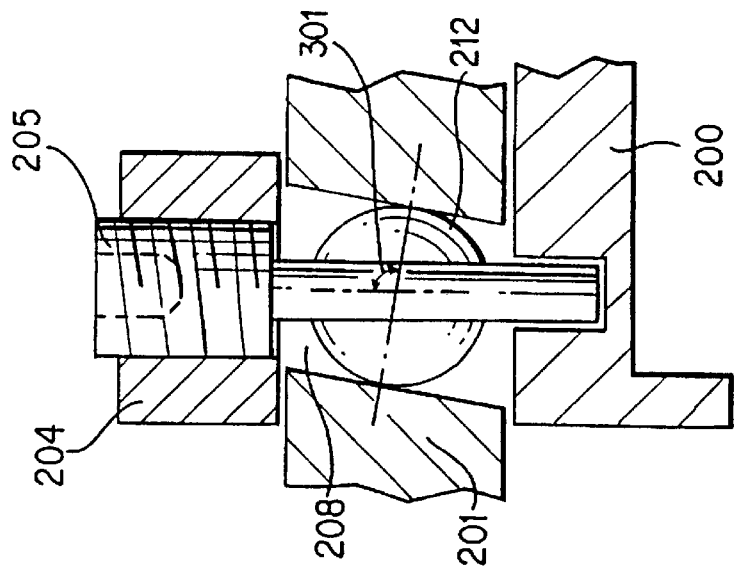
FIGS. 5A, 5B and 5C show a cross sectional view of a slot at three points of operation of the axial and rotational mechanism.
Figure 5B:
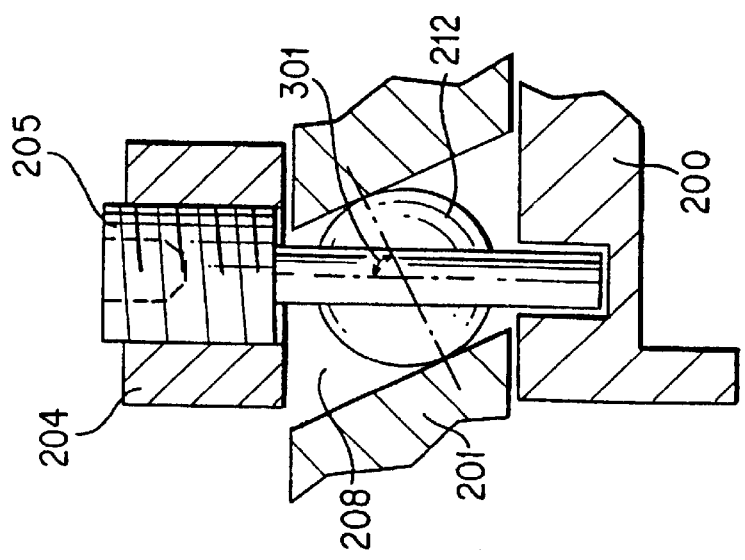
Figure 5C:
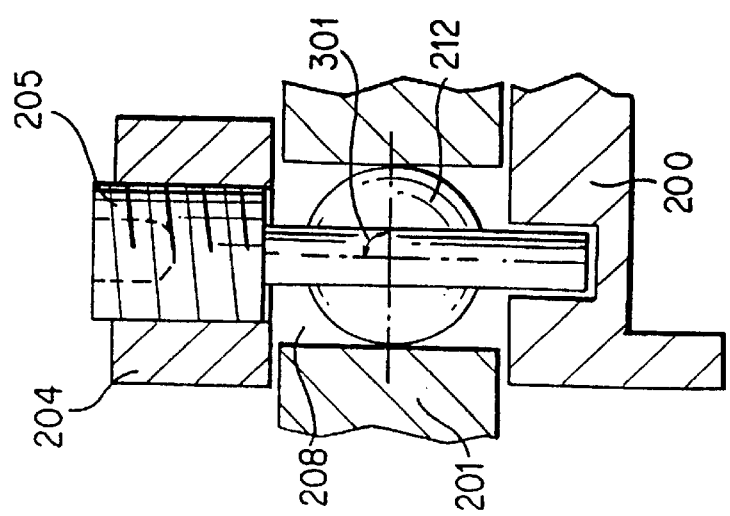

Using a conventional milling machine, the cylindrical housing 201 is mounted to the slide bed in a standard indexing head, with its cylindrical axis perpendicular to the axis of the tooling head. A slot saw of appropriate width and diameter is mounted in a common right angle fixture attached to the milling head, the arbor being parallel to the cylindrical axis of the housing, and the plane of the slot saw being perpendicular to the same. The right angle attachment is then rotated to a specified angle relative to the cylindrical axis of the housing. The center of the slot saw is positioned over the center of the housing using standard trigonometric methods. The slots 208 are then cut into the housing by raising the slide bed of the milling machine. Using a slot saw of an appropriate diameter and specifying the depth of the cut, produces the desired surface at each end of the slot that is nearly parallel to a radial line extending from the center of the cylinder. In this embodiment, where a total of three slots are specified, the remaining slots are cut by moving the housing 120 degrees and repeating the procedure until all slots are cut. As shown in FIGS. 5A, 5B and 5C, because the cut is made with a planar saw, the resulting slot 208 is considered pseudo-helical, that is, the sides of the slot are perpendicular to the cylindrical axis of the housing only at center point of the arc of the slot 208 as shown in FIG. 5A. As expected, perpendicularity is lost at an increasing rate from this center point towards either end of the slot 208 as shown in FIGS. 5B and 5C. The rate of this loss of perpendicularity is proportional to the specified helical angle of the slot. Normally, a simple, round connecting pin with a diameter equal to the width of the slot and held perpendicular to the cylindrical axis, would be utilized, connected to the focus grip ring 204 external to the housing 201 and engaging the movable cylinder 200 within. In that configuration, attempted rotational motion of the focus grip ring 204 and connecting pin from the center point of the slot 208 to produce a helical movement of the connecting pin, would immediately jamb the connecting pin in the slot due to this loss of perpendicularity. In this embodiment the loss of perpendicularity in the pseudo-helical slot 208 is compensated for, and true helical like motion in the slot is maintained, by using a connecting pin 205 with a smaller diameter than the width of the slot inserted into a ball 212 having an outside diameter equal to the width of the slot 208. As shown in FIGS. 5A, 5B, and 5C, in practice, as the focus grip ring 204 is turned and the connecting pin 205 travels through the slot 208, the points of continuous contact between the sides of the pseudo-helical slot 208 and the spherical surface of the ball 212 moves slightly through an initial angle 300 as shown in FIG. 5B and 5C that becomes perpendicular to the axis of the connecting pin 205 as the connecting pin reaches the center of the slot as shown in FIG. 5A. This introduces an inconsequential non linearity between the rotation of the connecting pin 205 through the pseudo-helical slot 208 in the cylindrical housing 201 and the axial movement of the focus grip ring 204 and therefore the moveable cylinder 200. As shown in FIGS. 5B and 5C, the value of this non-linearity 301 is calculated as the height of the circular segment by standard trigonometric methods. Within limits, this method of producing pseudo-helical slots or grooves can produce true helical motions with ordinary professional skills and tooling found in most modestly equipped model making and production machine shops. In contrast, the conventional method of introducing true helical slots or grooves in a cylinder requires unique equipment and skills, but can produce features that can be of nearly unlimited length, depth and width, and that preserve the perpendicularity of the sides of the slots or grooves relative to the cylindrical axis at any point along the cut.

In FIG. 1 the source 10 is mounted on the device 15. FIG. 4 shows the device 15 in detail consisting of a moveable, telescoping cylinder 200 within a stationary cylindrical housing 201, which is designed at one end 215 to mount and lock to the conventional male bayonet mounting surface of many common photographic lenses. The housing is further adapted at the mounting end to accommodate typical optical elements like an interference filter.

The source 10 is held securely within the moveable, telescoping cylinder 200 which can move axially (focus) and rotationally, along, and around the center axis of the stationary cylindrical housing 201. Focus and rotation of the source 10 are controlled by external annular grip rings 204 and 216 respectively that fit around the outside diameter of the stationary cylindrical housing 201, and are in contact with the moveable, telescoping cylinder 200 by way of pins 205 that connect the focus grip ring 204 and the moveable cylinder 200 through slots 208 in the stationary cylindrical housing 201 and that connect the rotational grip ring 216 and the movable cylinder 200 through the circumferengial slot 206 in the stationary cylindrical housing 201. A slot in the stationary housing, for rotational control of the moveable cylinder, located opposite the mounting end and in the telescoping area of the housing, is a circumferengial through slot 206T over a range of 180 degrees and an external counterbore groove 206C for the remaining 180 degrees.

Another circumferengial through slot 207, of at least 90 degrees range, that allows rotational control of a optical polarizer by way of a radial lever that extends from the polarizer, is located near the mounting end of the housing. Additional slots in the stationary housing, 208 for focus control of the moveable cylinder 200, are evenly spaced, pseudo-helical through slots, cut at an appropriate angle to the cylindrical axis of the stationary cylindrical housing 201 to provide the desired sensitivity and control of telescoping focus (axial) motion, and are located in the telescoping area of the housing between the mounting end 215 and the circumferengial through slot 206 for rotational control of the moveable cylinder.

The moveable cylinder 200 has an appropriately long axial slot on its outer surface for rotational control, and is engaged to the rotational grip ring 216, associated with the circumferengial through slot 206T and the circumferengial groove 206C, and is engaged to the focus grip ring 204, associated with the pseudo-helical grooves 208 of the housing. In practice, the external grip rings 204 and 216 are designed to slip fit onto the outside diameter of the cylindrical housing 201. Three equally spaced screw tapped holes 209 in each of the rings accept a threaded portion of the pins 205 that penetrate the cylindrical housing 201 and engage the moveable cylinder 200 in the appropriate slots and grooves. In the case of the rotational grip ring 216 for the moveable cylinder 200, one pin 205 extends through the circumferengial slot 206T of the cylindrical housing 201 and slidingly engages the axial slot 210 of the moveable cylinder 200. An additional two pins extend through the rotational grip ring 216 into the external counterbore groove 206C to provide stability and a means of locking its position.

In the case of the focus grip ring 204, three pins 205 penetrate the cylindrical housing 201, one through each pseudo-helical slot 208, and slidingly engage the moveable cylinder 200 in the circumferengial groove 211.

Source Polarization

Returning to FIG. 1, while polarization is optional, a more defined resonance is generated by 'p' polarized light impinging on the sensor. The amplitude of the resonance is inversely proportional to the extinction coefficient of the polarizer. Since the amplitude is large to start with (50–90%), a poor polarizer (0.1–0.01 extinction) is sufficient. Any of a number of devices including, linear polarizers, prism polarizers, polarizing beam splitters, retardation plates, Cornu pseudopolarizer, or Dichroic sheet polarizers can be used. As shown in FIG. 1 a dichroic linear film polarizer 20 with an extinction coefficient of $10^{-2}$, and 70% transmission @ 875 nm (Oriel 27361) is used for polarizing the light in the 'p' (II) direction.

Angle Scanning Means

Scanning the illumination angle may be done with variety of devices and techniques such as a goniometer, source or slit translation, rotating mirror or refractor scanner, an LED/Laser diode array at the focus of a lens, or a spatial modulator. Angle scanning may also be accomplished by mechanically moving a single source element to different locations that result in the source impinging on the sensor at different angles. This embodiment uses an array of LED's as the source 10 located at the back focal plane of the lens system 40. The array can be constructed with multiple tilted rows of LED's or straight rows and a tilted array, such that each LED is at a unique height above or below the optical axis, and with the center LED exactly on this axis. By doing this the light from each diode produces a collimated beam illuminating the sensor at an angle which varies with the height of each LED relative to the optical axis. The range of angles in the beam, $\Delta\theta_Y$, is given by the height of a diode divided by the focal length of the angle scanning lens system. The range of angles available is given by the height of the array divided by the focal length of the lens system 40. Finally, the step size of the angle is given by the diode spacing divided by the focal length of the lens system 40. Lateral displacements (sideways from the optical axis) will produce negligible resonance broadening. In this embodiment a Minolta 75–300 mm Zoom lens in combination with a Tamron 2×teleconverter is used as the lens system.

Pre-Dispersion Grating Angle Scan

Scanning the incident angle $\theta$ results in scanning the output angle $\theta°$ according to the grating equation:

$$\mathrm{Sin}\theta^i + \mathrm{Sin}\theta^o = \frac{m\lambda}{d}$$

$$\mathrm{Cos}\theta^i d\theta^i + \mathrm{Cos}\theta^o d\theta^o = \frac{m}{d} d\lambda$$

And for monochromatic light:

$$-\frac{d\theta^o}{d\theta^i} = \frac{\mathrm{Cos}\theta^i}{\mathrm{Cos}\theta^o}$$

Pre-Dispersion Grating Wavelength-angle correlation

To generate a narrow resonance using a polychromatic source, the sample has to be illuminated at a different resonance angle for each wavelength in the light source spectrum. The relationship between the wavelength and the angle defines the resonance dispersion curve. The slope of this curve is the resonance dispersion ($R_{Disp}$). One way to achieve this, is by using an optical grating with the same dispersion, oriented correctly between the light source and the sensor. Determining the optimal optical grating requires examining the grating equation above.

From this the angular dispersion can be calculated, which should be equal to $R_{Disp}$:

$$\cos\theta^i d\theta^i + \cos\theta^o d\theta^o = \frac{m}{d} d\lambda$$

$$\frac{d\theta^o}{d\lambda} = \frac{m}{d\cos\theta^o} = SPR_{Disp}$$

Knowledge of the theoretical $R_{Disp}$ allows the determination of the groove spacing- d, and the output angle- $\theta^°$ for the optical grating, in a given diffraction order- m which yields maximum diffraction efficiency. After choosing d and $\theta^°$, the light input angle for the grating can be calculated:

$$\sin\theta^i = (SPR_{Disp} * \cos\theta^°) \cdot \lambda - \sin\theta^°$$

Additional considerations are that: a reflection grating as well as a transmission grating can be used; for a reflection grating, $\theta^i$ and $\theta^°$ should be far apart, to allow the placement of additional optics without vignetting; for a transmission grating, any combination of angles will work; diffraction efficiency should be maximized for the polarization required by the resonance sample. In this embodiment, the resonance peak is observed by scanning the illumination angle for each wavelength around the resonance angle.

Figure 6:
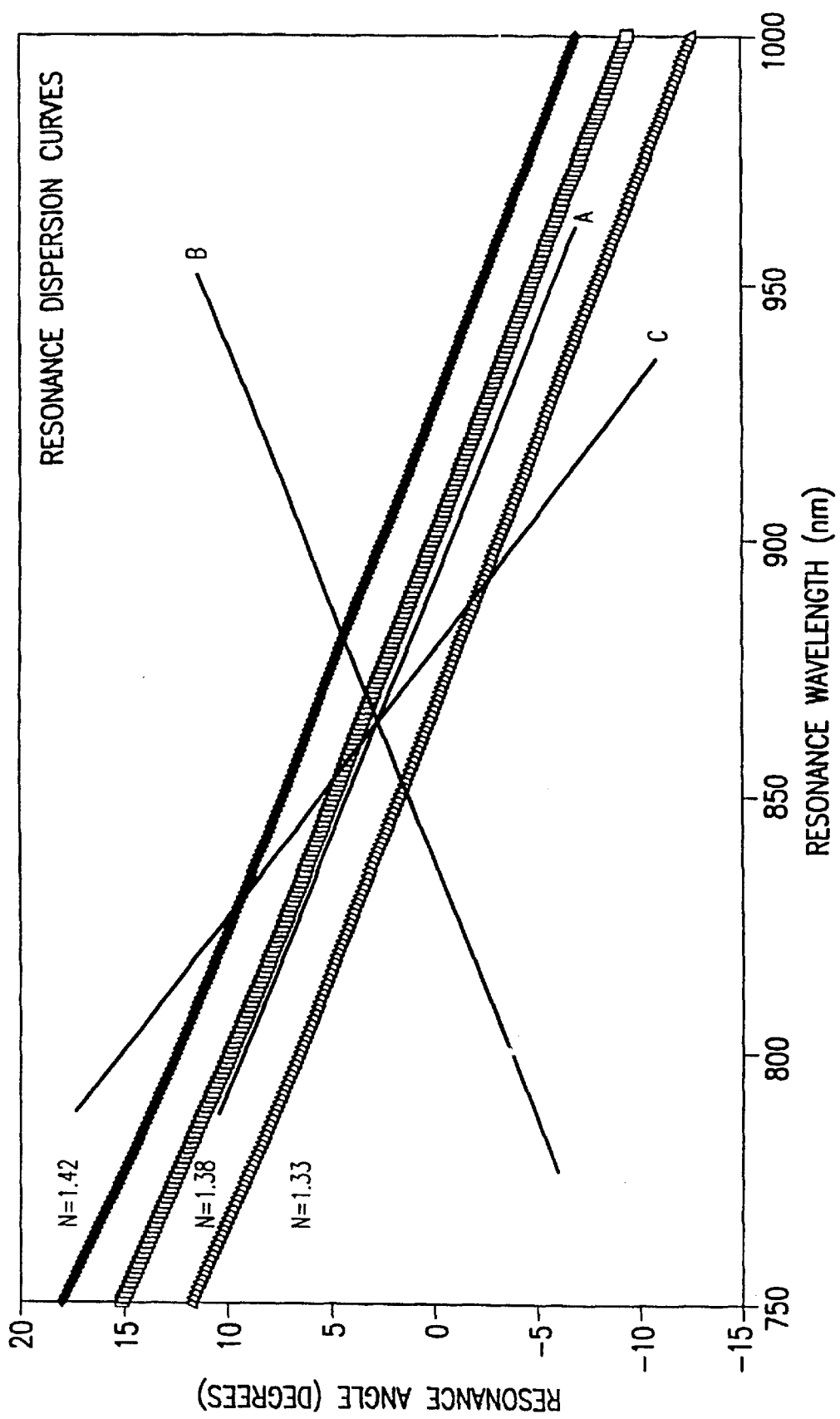
FIG. 6 shows resonance dispersion curves for various conditions.

In FIG. 6 the resonance dispersion curves for the SPR sensor described below are shown at 3 different indices of refraction (n=1.42, n=1.38, n=1.33). Also three "Scan Lines" (A, B, C) are shown. Line A describes a pre-dispersion grating designed to closely match a section of the dispersion curve at a particular index of refraction. In the embodiment of FIG. 1 we measure the resonance simultaneously at all the points on line A, and in order to scan the resonance, the whole line can be shifted in angle (angle scan). The advantage of this method is that the resonance is measured along a continuous set of wavelength-angle pairs, so that the total signal is increased. In the case of two dimensional imaging, each two dimensional active site on the sensor is mapped to a group of pixels in the CCD camera, and the signal on those pixels will change with the angle.

In FIG. 1 a 1200G/mm Kaiser Optics (HG-875-31-40) holographic transmission grating is used as the pre-dispersive grating 50 for dispersing the 830–910 nm wavelength range to match the resonance angles. The transmission of this grating for 'p' polarized light is around 90%.

An 875 nm/10 nm(fwhm), 65% transmission interference filter 30 (Oriel 59495) is used for filtering off-resonance wavelength/angles portions of the source spectrum, to achieve a better dispersion matching, and narrower resonances.

Lines B and C on FIG. 4 describe a pre-dispersion grating which does not compensate for sensor dispersion, but is useful for alternative embodiments (below). The advantage of this method is the coverage of a range of indices of refraction but at the expense of signal. The difference between B and C is in the range of angles and wavelengths that are covered by the pre-dispersion grating which in turn determines the requirements of the optical system that is used to image the sensor on the detector.

Sensor

The sensor shown in FIG. 1, 60 in this embodiment is a grating coupled surface plasmon device with a 854.5 nm groove spacing. The resulting resonance angle at 875 nm and n=1.33 is 20 deg. A planar waveguide or multi-layer planar waveguide may also be used.

A 2D array of sites derivatised/sensitized??? with the same sample can be used for the analysis of multiple assays. A 2D array of sites with different samples can be used for the analysis of a single assay Detection System As shown in FIG. 1 light rays are usually reflected from the sensor 60 with their angle of reflection equal to their angle of incidence. Thus the rays will typically span a small range of angles in the perpendicular plane, with the central angle to the sensor being $\theta_r$. It is convenient to take the ray coming from the center of the sensor at an angle $\theta_T$ and $\theta_A=0$ as the optical axis of the detection system. Imaging on the detector is obtained with a single, high quality, lens 70 oriented nearly normal to the optical axis and the detector making an angle of very nearly—$\theta_T$ with the optical axis. The entire system has a symmetry plane that is perpendicular to the orientation of the sensor. This embodiment utilizes a Meles Griot part number LAI007 achromatic lens (60 mm focal length) positioned equidistant (117.16 mm) from the sensor and the detector for $\theta_T=14°$, and tilted –0.49° with the detector tilted –14.08°. With this design, there is a variation in magnification across the detector along the symmetry plane of about 3% when a 1 cm square sensor is used. This configuration allows an array of 100 by 100 samples on a 1 cm square sensor to be resolved. Another type of lens that can be utilized in this embodiment is Rolyn part number 22.0162, having a 60 mm focal length, and a 30 mm diameter. Using a $\Delta\theta_T$ of 5°, an array of 50 samples in the parallel direction, and 25 samples in the perpendicular direction on a 1 cm square sensor can be resolved.

The size of the detector array can be minimized by demagnifying the image on it, but at the expense of a longer optical path than that for one-to-one imaging, and a larger diameter lens. Demagnification will also be limited by the need to have a length of at least a few pixels per sample for adequate resolution. Alternatively, the image can be magnified in order to get more pixels per imaged sample. Up to a certain point, a long focal length will make the optical path closer to paraxial and thus less demanding. The optical limitations on the sample density are image quality and pixel density. Imaging lens 70 may also be a curved mirror where a one dimensional array detector is used. The detector can be positioned so that the blurring along the line connecting the images of the individual sample bars is minimized so that any astigmatism will not have a significant effect.

When high wavelength or angle resolution scanning of the sensor resonance is required the resulting light/signal levels can be very low (compared to the detector and system noise levels). The preferred mode of operation in this case is to always be signal shot noise limited, which means that all the other system noise sources should be minimized. In the case of CCD, PDA, or CID detectors, this means that the pixel-wells should be filled with photoelectrons within the exposure time, and the dark-current, electronic read noise, and digitization noise should be minimized. To increase the signal levels, one can image a range of resonance wavelength/angle pairs on the detector, but that imposes the requirement of additional scanning. Dark current of the detector can be lowered by cooling, and the electronic read noise can be minimized by the well known CDS (correlated-double sampling), and MPP (Multi-phase pulsing) electronics, and the use of 'quiet' electronic components. In the case of digital cameras, the digitization noise can be minimized by increasing the effective number of A/D bits, or by dithering and averaging the signal.

According to this embodiment, a 30 frames per second, 10 bit, Kodak digital CCD camera can be used. This camera uses a 1K×1K silicon CCD chip, and can fully image a 10×10 mm sensor at unity magnification. The quantum efficiency of the silicon CCD is about 10% @ 875 nm. The integration time of the camera should be chosen such that the pixel wells are nearly filled in that time (signal shot-noise limited), and the frame rate is chosen to match the chemical reaction time scale.

Sequential Resonance Detection

In this embodiment the sensor is illuminated with a beam of light having a sufficiently small range of angles at each wavelength such that it will generate a sharp resonance. The angle is scanned as a function of time so as to sequentially trace out the resonance for the different active sites having different values of the sample refractive index. The resonance refractive index thus varies monotonically during the scan. The sensor is imaged onto a detector that has dimensions corresponding to the sample array. The outputs of the detector pixels are recorded as a function of time. When the incident light is on resonance for a particular sample, the pixels onto which this sample active site is imaged will show a decrease in intensity. From the parameters of the incident light and the detector intensities versus time, the resonance position and hence the effective index of refractive index for each sample in the array can be determined.

To normalize against the optical transmission of the system, the polarizer (???) is set such that the polarization of the light incident on the sensor is parallel to the sensor grating grooves ('s') such that no SPR is generated. The reflected intensity is recorded (in computer memory for example) for each element in the source array. Then the polarizer is set such that the polarization of the light incident on the sensor is perpendicular to the sensor grating grooves ('p') and an SPR is generated. For each element in the source array the reflected intensity is measured and divided by the corresponding pre-recorded intensity. This results in a normalized resonance peak, which can be used for further quantitation. To correct for detector dark current, a dark exposure is recorded, when all the elements in the light source are turned off. This dark reading is subtracted from any other measurement.

The read rate of the array is set relative to the scan rate of the illumination beam so as to take at least five to ten readings across a typical resonance. The scan rate of the illumination beam is set so that each reading of the array integrates enough light for adequate S/N without risking saturation. In general, two dimensional array systems take better advantage of the available light than do one dimensional array systems.

Embodiment with Anamorphic Optical Design

Figure 8:
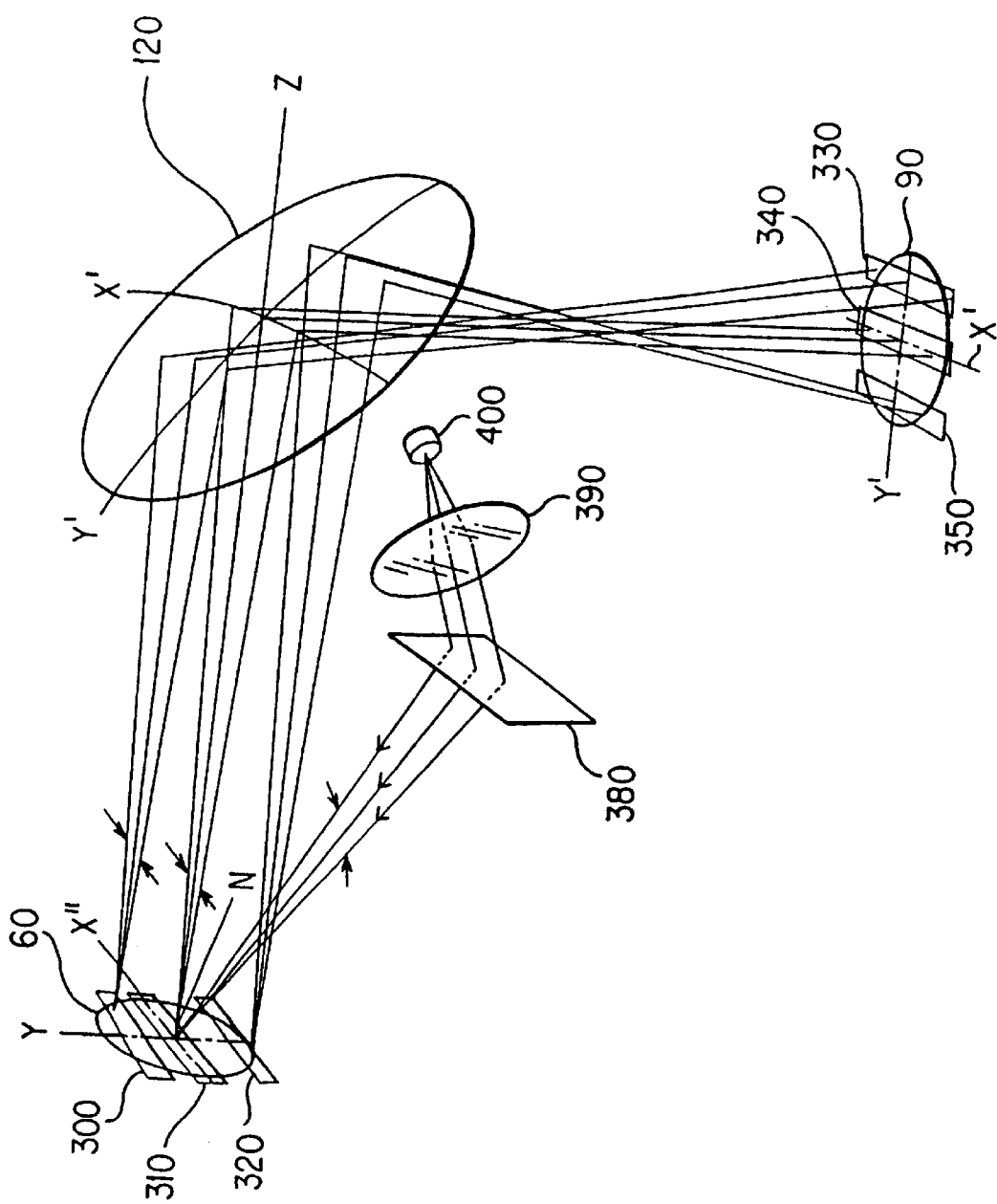

FIG. 8 shows an additional embodiment of the invention. The light source 10 in this embodiment comprises a light emitting element 370 and a collimating lens 360. The light emitting element is an extended monochromatic or quasi-monochromatic source such as a filtered gas discharge lamp or a diffused laser diode. In FIG. 8 light from the source 10 is directed toward a sensor 60 over a range of angles sufficient to cover all possible resonance positions. The sensor surface is divided into a one dimensional array of active sites 300, 310, 320. The light reflected from the active sites on the sensor on planes parallel to the x"-z plane impinges on an anamorphic optical system 120 which then directs the light to a two dimensional detector array 90. In this embodiment, the focal length of the anamorphic imaging system is different in two orthogonal planes. Using this technique allows the system to image angles reflected from the sensor in the perpendicular plane, and the active site array in the parallel plane along the y axis. Active site 300 is imaged to zone 330 on the detector. Within this zone angles are displayed along the x' axis on the detector 90, Similarly site 310 is imaged to zone 340 and site 320 is imaged to zone 350. To achieve this, the detector must be at the focal point of the imaging device in the perpendicular plane. The focal length of the imaging device in the parallel plane and the distance from it to the sensor are selected so that the sensor is imaged at the detector. The focal length in the parallel plane must be significantly less than that in the perpendicular plane.

The anamorphic lens system 120 can be a single lens, a combination of a standard lens and a cylindrical lens, or a spherical mirror which has a natural astigmatism when used off axis. If, for example, the mirror is tipped at a 45° angle to the optical axis, about an axis in the perpendicular plane, as in FIG. 8, the focal length in the perpendicular (sagital) plane will be twice that in the parallel (tangential) plane.

As the index of refraction of the solution or sample for each active site changes, the corresponding resonance will move along the angle axis on the detector, ie along the x' axis.

FIG. 8A, shows a similar embodiment, where source 10 comprises a polychromatic point source 400, collimating lens 390, and anti-correlation grating 380. The anti-correlation grating produces a pre-dispersion corresponding to curve B in FIG. 6. In this way the different wavelengths in the bandwidth of source 400 impinge on the sensor 60 at angles which accentuate rather than compensate for the resonance dispersion in the sensor. Thus, resonance position shifts on the sensor 90 are enhanced over those of a simple wavelength or angle dispersive system.

In the embodiments of FIGS. 8 and 8A, the entire set of sample resonances is captured in one array detector exposure. This improves resonance detection accuracy by eliminating effects of source fluctuations and/or system drifts.

Peak Shift Estimation with Derivative Fitting

Model Peak

In surface plasmon measurement, a peak is obtained that typically has a dip over a sometime sloped baseline. When the measurement is performed on another sample at a different concentration, this dip will shift depending on the change in refractive index corresponding to concentration difference between the two samples. The concentration can then be predicted using a calibration model relating the peak shift to concentration. The algorithm to be used for peak shift calculation using the two peaks calls for a model peak to begin. The model peak is an x-y pair representing the shape and location of a reference peak from which all actual peak locations are to be measured. This model peak can be obtained through theoretical calculation which has the advantage of being free from all baseline effects. If the model peak is to be obtained with a blank sample before real sample measurement or at the same time as the real sample measurement in a different channel, the measured reference peak needs to be processed for noise and corrected for baseline effects, if necessary. The measured model peak can be smoothed through Savitzky-Golay digital filtering with a filter that is smaller than the resonance width to insure no peak distortion. If it is expected that the baseline of the reference peak will follow a different shape (e.g., a polynomial of different order) from that of an unknown peak, baseline correction needs to be performed on the reference peak by, for example, fitting a low order polynomial to both ends of the reference peak and subtracting it from the same peak. It is not necessary to perform the baseline correction even if the baseline is different between the reference and an unknown peak as long as the two peaks follow a baseline model of the same form such as a polynomial of the same order. The reference peak after this pre-processing (noise filtering and possibly baseline correction) is called model peak and will be used to determine the relative shift of an unknown peak.

Peak Shift Calculation

Assuming a first order model for the baseline of the unknown peak, the following (4×m) matrix can be constructed:

$$X = \begin{bmatrix} 1 & 1 & p_1 & \left(\frac{dp}{d\lambda}\right)_1 \\ 1 & 2 & p_2 & \left(\frac{dp}{d\lambda}\right)_2 \\ \vdots & \vdots & \vdots & \vdots \\ 1 & m & p_m & \left(\frac{dp}{d\lambda}\right)_m \end{bmatrix}$$

where the first column is composed of ones to account for a vertical offset, the second column is composed of the series 1, 2, . . . , m, to represent the tilt of a baseline, the third column represents the model peak with intensities at m different wavelengths or angles, and the last column is the first derivative of the model peak which can be computed with a Savitzsky-Golay filter of proper order and size.

When an unknown peak y (dimensioned m×1) is obtained from an $$y = \begin{bmatrix} p_{1,u} \\ p_{2,u} \\ \vdots \\ p_{m,u} \end{bmatrix}$$

unknown sample, a multiple linear regression in the form of $$y = Xb + e$$

can be performed to obtain a set of 4 regression coefficients in b (4×1) as $$\Delta\lambda = \frac{b_4}{b_3}$$

$$\hat{b} = (X^T X)^{-1} X^T y$$

where the vector e (the same dimension as the unknown peak y) is the model error, the first two coefficients ($b_1$ and $b_2$) in b represent the zeroth and first order terms for the baseline, and the third coefficient $b_3$ represents a relative scale in peak intensity (or attenuation) between the unknown and the reference sample. The shift of the unknown peak with respect to the model peak can be calculated by taking the ratio between the fourth and the third coefficient The shift thus calculated will be in units of wavelength or angle spacing in y (consistent with the unit with which the derivative is calculated). This shift in either wavelength or angle can then be related to sample concentration through a calibration procedure. It should be mentioned that the most computationally expensive part, $(X^T X)^{-1} X^T$, only needs to be calculated once and stored for repeated applications to successive unknown measurements y without re-computing it every time when an unknown sample is measured.

When the shift is large, for example, larger than ½ of the sampling interval, it may be necessary to refine the derivative calculation by pre-shifting the unknown peak y according to the first shift estimate so that it becomes closer to the model peak for a second and improved shift estimate. The pre-shifting can be accomplished through proper interpolation such as spline interpolation. It usually takes less than 5 iterations to achieve satisfactory shift estimation.

While a first order baseline model is assumed here with a corresponding four-parameter linear regression, any other proper model for the baseline can be assumed with a either linear or nonlinear regression. The same basic principal nonetheless applies to the shift calculation.

Embodiment Utilizing Wavelength Scanning

Figure 2:
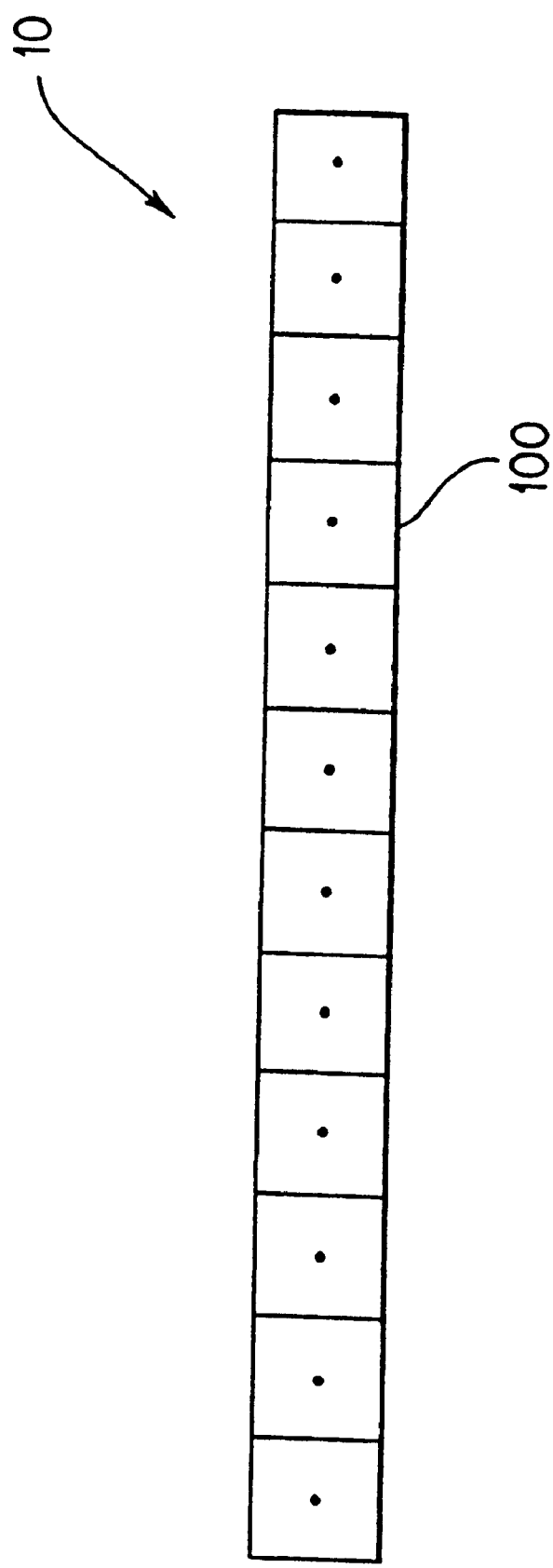
FIG. 2 shows an example of a one dimensional array of light sources.
Figure 9:
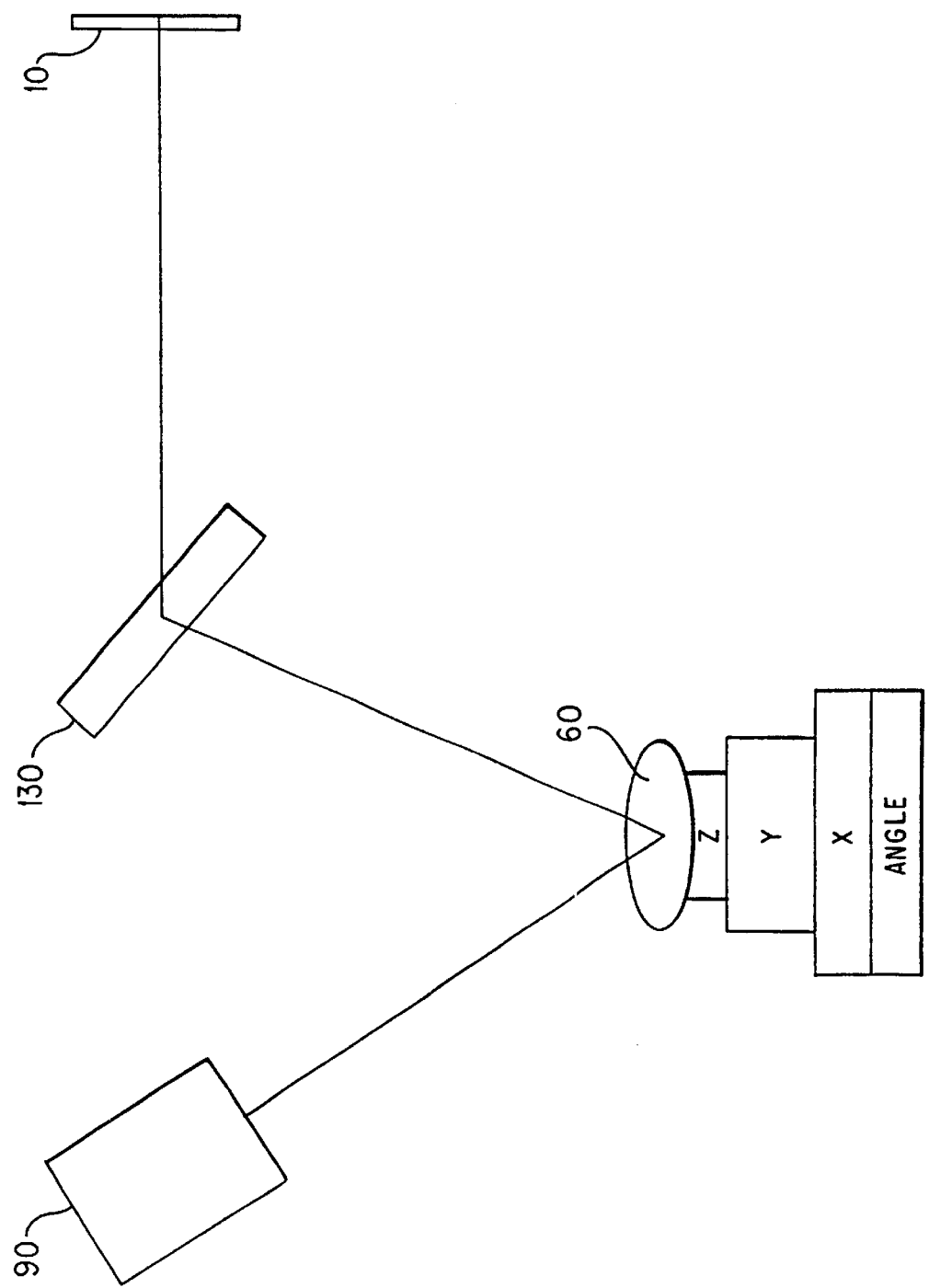
FIG. 9 shows an additional embodiment of the invention.

FIG. 9 shows an embodiment of the invention directed toward wavelength scanning. Light emitted from the source 10 travels through an optical system 130 and impinges on a sensor 60. Light reflected from the sensor 60 then travels the detector 90. The wavelength scanning means may comprise the optical system 130 which may be a spectrometer, a grating, an acousto-optical tunable filter, a Fabrey-Perot or Fourier transform interferometer, a liquid crystal filter, a tilting dielectric filter, a linear variable filter, a Lyot filter, or a tunable laser. Alternatively the wavelength scanning means may comprise the source 10 and the optical system 130, where the source is a linear array as shown in FIG. 2 or a two dimensional array as shown in FIG. 3 and the individual elements of the array produce different wavelengths. In this particular embodiment the optical system 130 serves to focus the different wavelengths onto appropriate areas of the sensor.

ADDITIONAL MATERIAL

Design Considerations for a Conventional Grating Spectrometer System:

The light throughput will be proportional to the solid angle of the illumination beam, the wavelength increment from the monochromator, and the size of the sample sites.

The solid angle of the illumination beam is pi times $\Delta\theta_T$ times $\Delta\theta_L$ (both in radians).

$\Delta\theta_T$ in radians equals the monochromator slit width divided by the focal length of the imaging lens, L1.

The wavelength range is the product of the slit width and the dispersion of the monochromator.

$\Delta\theta_L$ in radians is the product of the focal length of lens L1 and the slit height. This angle can be increased up to the point at which it degrades the imaging on the detector to the point where adjacent samples are insufficiently resolved.

Presumably the grating of the monochromator is imaged onto the SPRG. The size of this image on the SPRG will be the size of the grating times the focal length of L1, divided by the length of the monochromator.

All this implies a small, low resolution monochromator. For example, assume that the SPRG is 1 cm high, the desired wavelength range is 2.5 nm, and the desired SPR angle range is 0.15 deg., and the focal length of L1 is 5 cm. A 5 cm monochromator with a dispersion of 10 nm/mm a 0.25 mm slit width, and a square grating a bit over 1 cm would suffice.

For a tunable laser system, step tunable is adequate as long as the minimum steps are not too large.

Illumination Systems

When discussing light incident on (and reflected from) the sensor, directions are relative to the grooves of the grating. The direction along the length of the grooves is referred to as parallel, and the direction across the groves is referred to as perpendicular. It is also useful to define two orientations of planes: Perpendicular plane refers to any of the planes which are perpendicular to the grating lines. Parallel plane refers to any of the planes which are parallel to both the grating lines and the optical axis. The angle of incidence of a ray on the grating is described in terms of two projections. $\theta_T$ is the angle of incidence in a perpendicular plane. This angle is typically 10° to 20°. $\theta_L$ is the angle of incidence in a perpendicular plane. This range of this angle is a few degrees which are centered on zero. The ranges of these angles incident on the sensor are $\Delta\theta_L$ and $\Delta\theta_T$, respectively. The wavelength of the illuminating light is denoted $\lambda$. It has a range of $\Delta\lambda$. A general requirement of all the illumination systems described below is that the sensor is illuminated uniformly, especially in regard to the value(s) whose range is tightly restricted ($\Delta\theta_T$ and/or $\Delta\lambda$). $\Delta\theta_L$ should have a relatively large value for good signal to noise. The limit on its range is insufficient resolution of adjacent samples on the sensor. This is caused by aberrations in the detection system optics.

Fixed Monochromatic Source, Variable Angle

In this embodiment the sensor is illuminated with a beam of light that has a narrow wavelength range, $\Delta\lambda$, and a narrow range of angles in the perpendicular direction, $\Delta\theta_T$. The ranges are selected so that they are no more than approximately one third to one half of the anticipated width of the resonance in order that the measured resonance is not made too broad. The minimums of these ranges are selected to maintain an acceptable signal to noise ratio. For a typical example $\Delta\lambda$ is approximately 2 nm and $\Delta\theta_T$ is approximately 0.1°. $\theta_T$ is scanned over a sufficiently wide range so that the resonance can be clearly seen and its angle precisely determined for all desired values of sample refractive index. A typical range is approximately 5°

Fixed Angle, Variable Wavelength/Frequency

In this embodiment, the sensor is also illuminated with a beam that has narrow ranges for $\lambda$ and $\theta_T$, and a larger range for $\theta_L$. The same considerations apply in selecting these ranges. The difference is that $\theta_T$ is fixed and $\lambda$ is scanned.

Monochromatic Source, Wide Angle Range

In this embodiment the wavelength range is again narrow, and the wavelength is fixed. The range of $\theta_T$ is made large enough to encompass all values required to measure the resonances expected for the desired range of refractive indices using the selected monochromatic wavelength. Means for achieving this illumination include using a source which emits over an adequate range of angles, a means of selecting a narrow band of wavelengths, and a means of imaging the source onto the sensor.

With a broad band source, a monochromator is used obtain a narrow band of wavelengths. The exit slit would be imaged onto the sensor. This is best suited to a 1-D arrays of samples due to the shape of a slit. With a low pressure discharge lamp, a narrow line could be isolated with a narrow band filter. A diode laser would not need any means of monochromation.

The imaging will most likely be accomplished with one or two lenses. While one lens will often be adequate, two lenses with a collimation zone in between them would be useful with a filter. The image of smaller sources must be magnified in order to illuminate all of the SPRG. Imaging could also be accomplished with a curved mirror.

A diode laser is another possibility.

All of these methods involve some tradeoffs. A broadband or multi-line source has a distinct disadvantage relative to Fixed angles Wide wavelength/frequency range due to the fact that most of the energy from the source must be discarded. As for diode lasers, their low etendue makes it difficult to illuminate a multisample SPRG over a wide range of angles, however, this may be overcome with high energy.

Fixed Angle, Wide Wavelength/frequency Range

For this illumination method the perpendicular angle range, $\Delta\theta_T$, is narrow and its central value is fixed. The wavelength range is made large enough to encompass all values required to measure the resonances expected for the desired range of refractive indices using the selected $\theta_T$. This is about 50 nm for the typical experiment outlined above. There are several possible means of achieving this illumination. What is required is a source that emits over a sufficiently broad wavelength range and a means imaging such as a lens. The source is placed in the focal plane of the lens (generally at the focal point) so as to produce a collimated beam. The angular range of the illumination in radians will equal the width of the source divided by the focal length of the lens. Because $\Delta\theta_L$ should ideally be several times larger than $\Delta\theta_T$, an elongated source would be beneficial.

Any of the broad band sources listed below could be used.

A simple, inexpensive, and effective means is to use a high brightness LED placed at the focal point of a lens.

A curved mirror could be used instead of a lens.

This method has the advantage that much of the source output is used, especially in the case of the LED. It therefore seems preferable to the above.

Conventional Single Channel Wavelength or Angle Scanning

1-D site Array Systems

A.1. 1-D Site Array Imaging Without Angle or Frequency Discrimination

The Wavelength/angle correlation method described above is used to illuminate the 1-D array of samples with all wavelength/angle pairs in the selected wavelength range which are on resonance for one particular sample refractive index in the selected range of sample refractive indices. The angle of incidence of the illuminating light varies in the plane perpendicular to the lines of the SPR grating on going from one wavelength/angle pair to the next. The illuminating light is scanned so as to scan through the refractive indices, with each of the wavelength/angle pairs being in resonance for the same refractive index at any one time. The light reflected from the SPRG is then focused onto the 1-D array detector in such a way that an image of the SPRG is formed on the detector. Good from the point of view that it utilizes all the light from a conventional source such as an LED. Bad in that it is subject to source-to-source variations (for source array version) or requires source translation. Relative to the 1-D simultaneous extraction methods, it takes a bit longer due to the need to scan, but it uses a much cheaper (1-D vs. 2-D) array and standard vs. anamorphic optics.

A.2. 1-D Site Array Imaging with Scanning Monochromator

This method uses Fixed angle, scanning wavelength/frequency illumination, which could use any one of several Wavelength Scanning Means. If a scanning monochromator is used, the exit slit of the monochromator is in the focal plane a lens, L1, which collimates the monochromatic light. The SPRG is place in the other focal plane of L1. It is oriented so that the collimated beam strikes it at the desired angle and so that the lines of the SPR grating are parallel to the exit slit of the monochromator. This arrangement will also form an image of the monochromator grating onto the SPRG. A second lens, L2, or other imaging means, collects the reflected light and forms an image of the SPRG on the linear array detector.

Advantages and disadvantages relative to the above system:

The previous system has an advantage in S/N or in data collection time resulting from the fact that the SPRG is illuminated with much more light. This results from the fact that each wavelength increment in the desired range is used at all times. In the example mentioned above, which considers a refractive index range of 1.32 to 1.38, the illumination is greater by a factor of about 20.

One advantage of the present system is that the illumination system is somewhat simpler. (this may be subjective) Another is the much narrower range of angles $\Delta\theta_T$ that the collection optics must handle. This may (depending on $\Delta\theta_L$) allow a smaller diameter lens for imaging the SPRG onto the detector and should lead to less blurring of the image. The latter will allow a higher sample density.

A.3. 1-D Site Array Imaging with Scanning Angle Discrimination

In this method, the SPRG is illuminated by the Fixed Monochromatic, scanning angle method. The SPRG is configured and oriented as in section A.1. The angle that the incident light beam makes with the SPRG is also varied as in A.1. The reflected light is collected and measured as in sections A.1. and A.2.

Comment: If a suitable laser diode array is available, this method is rated similar to A.1. If not, method A.2 seems preferable. There is more experience with scanning wavelengths than angles: thus this seems easier. Further more, the shape of a slit is well suited to generating the desired parallel and perpendicular ranges of angles. Finally, imaging for a range of wavelengths at fixed angle is easier than imagining for a range of angles at fixed wavelength, as is discussed above.

A.4. 2-D Site Arrays Imaging without Angle or Frequency Discrimination

This method is similar to A.1., with the following modifications:

Samples are arranged on the SPRG in a two dimensional array. This allows more samples to be measured in a single experiment. One price paid is lower S/N or longer read times due to the smaller size of the samples, whose shape will now be more like a dot than a bar. Another is greater hardware expense. The appropriateness of these added costs will depend on the sample volume.

This requires a two dimensional detector: this restricts it to a CCD.

Imaging must be good in all planes.

A.5. 2-D Site Array Imaging with Scanning Monochromator

Similar to method A.2., with the modifications listed for A.4.

A.6. 2-D Site Array Imaging with Scanning Angle Discrimination

Similar to method A.3., with the modifications listed for A.4.

Simultaneous Resonance Extraction

These methods differ from those in section A. in that they require the dimensionality of the detector to be one more than that of the sample, they require anamorphic imaging with a 1-D sample array, and the discrimination between angles, wavelengths, or wavelength/angle correlated pairs is made on the reflected light.

B.1. Single Channel Wavelength Dispersive (1-D Array Detector)

The sample is illuminated by the Fixed angle, wide wavelength/frequency range method. For any wavelength, the beam geometry is similar to that of method A.2. Typically, the source is at one focal point of the illumination lens and the SPRG is at the other focal point.

The reflected light is collected and focused onto the entrance slit of a polychromator. One possibility is to use a standard lens situated so that the SPRG is at one of its focal points and the entrance slit is at the other. An image of the source is thus formed on the entrance slit, which should be parallel to the SPR grating lines. Another is to use anamorphic imaging, with the SPRG imaged onto the slit in the parallel plane. The polychromator employs a linear array detector. The full spectrum, including the resonance, is captured in one readout of the array.

Method A.2. uses similar hardware components to read one wavelength from many samples simultaneously. This method reads many wavelengths from one sample simultaneously. Thus this method permits using a larger sample for better S/N. One advantage of A.2. is that it is easier to change wavelengths than to change SPRGs. Another is that reference "samples" can be included. Furthermore, A.2. is tolerant of orientation changes of the SPRG, while B.1. is not. These advantages will likely make A.2 better for detecting small differences in refractive index between samples, or between sample and reference. A.2 has the disadvantage of more moving parts (or other complexities) associated with wavelength scanning. Compared to A.1., this method uses an LED source just as efficiently, and has no moving parts. A.1. has moving parts, takes longer to read the SPRG, but has the very large advantage of many samples at once.

B.2. Single Channel Angle Dispersive (1-D Array Detector)

The SPRG is illuminated by the Monochromatic, wide angle range method. The angles reflected off of the SPRG are imaged onto a linear array detector so that the angles in the perpendicular direction, $\theta_T$ are spread out along the array. The simplest way to do this is to use a conventional lens with the array in its focal point on the opposite side from the SPRG, and the SPRG is ideally at other focal point of this lens. This has the disadvantage that a wide $\theta_L$ range requires an impossibly tall detector. This is corrected using anamorphic imaging, which is discussed above.

This method seems less efficient than B.1. This is due to the general disadvantages of the Monochromatic, wide angle range method relative to the Fixed angle, wide wavelength/frequency range method as discussed above. It also suffers due to the need to image a relatively wide range of angles onto the detector.

B.3. Single Channel Correlation Dispersive (1-D Array Detector)

In this method, the SPRG is illuminated with sufficiently broad ranges of both wavelengths and angles so that there are a large number of correlated pairs for each anticipated refractive index. This is achieved by imaging a white light source onto the SPRG. An LED would likely be ideal in terms of price/performance and efficiency. If the SPRG is larger than the source, the source image can be magnified without any loss as long as the required range of angles is still present in the illuminating beam. The detection system is essentially the Wavelength/angle correlation method of illumination operated in reverse by replacing the array of source diodes with the array detector. The discussion of the advantage of anamorphic imaging onto the detector in the above section applies here as well.

This method is certainly more efficient than ether of the above two due its simultaneous use of all wavelengths and angles. It is also likely to be trickier to align. If this is so, the question is whether the signal to noise advantage is worth the extra effort.

B.4. Single Channel Anti-correlated Illumination (1-D Detector)

Illuminating light uses a grating as in method A.1., but in a different orientation. Angles and wavelengths are paired up so that one pair is on resonance for each refractive index in the range of interest. Anamorphic detection optics. Would seem to be as good as A.3.

B.5. 1-D Sample Array with Wavelength Dispersion (2-D Array Detector)

Similar to B.1, but with a 1-D sample and a 2-D spectrometer detector. Wavelengths are imaged in the perpendicular plane of the detector and samples in the parallel plane. Anamorphic optics are essential.

Comparison with A.1: Utilize light from source equally well. A.1 should be less expensive due to 2-D detector in B.5. B.5. avoids problems of multiple or moving source.

B.6. 1-D Sample Array with Angle Dispersion (2-D Array Detector)

Similar to B.2, but with a 1-D sample array and a 2-D detector array. In this case, anamorphic imaging of the SPRG on lo the detector is essential for separating both angles and samples on the detector. With a high intensity laser diode source, this should be better than B.5 due to simpler optics.

Anamorphic lens implementation
Off-axis spherical mirror implementation

B.7. 1-D Correlation Dispersion (2-D Array Detector)

Similar to B.3, but with a 1-D sample array and a 2-D detector. Optics more complicated than B.6. Worth it if a sufficiently intense source is available.

B.8. 1-D Sample Array with Correlated Dispersion (2-D Array Detector)

B.9. 2-D Sample Array with Micro-resonance Display (2-D Array Detector)

Subdivide the CCD into zones, each displaying a small linear resonance curve associated with a particular sample/site. Could either be angle or wavelength (or even correlated) resonance display. Requires a site selection mask or lenslet array. Mask located in SPR conjugate plane, detector in angle conjugate plane, eg. Disadvantage: needs alignment between consumable sites and reader optics mask.

Other Considerations

Front vs Back Sensor Illumination

Front illumination procedure, light from a window to an air (or sample) gap between window and gold grating, is equivalent to the Otto configuration of the attenuated total reflection coupling technique. On the other hand, the back illumination procedure, light coming from a plastic or glass substrate to pass through the gold layer of the grating then to face the sample layer, is equivalent to the Kretschmann configuration of the attenuated total reflection coupling technique. Although the front illumination requires a good light transmission through the sample, the back illumination requires a good light transmission through the metal grating. In order to design suitable gratings for the front and back illuminations, we have performed the spectral simulations by changing the thickness of the sample layer and the metal layers including a underlying metals such as Aluminum.

Wavelength Selection

In a spectroscopy with a given absorption band, the detection sensitivity is higher when the linewidth is narrower. For a grating coupled surface plasmon resonance, as expressed by eq (10), the FWHM is proportional to $k_i$, wavelength and a reciprocal of the cosine of the incident angle. Thus, the shorter wavelength is preferred from the wavelength dependence. However, it is clear from the calculation based on eq (1), $k_i$ is smaller at longer wavelength. As a result, it was calculated that the half-angle width of the grating-coupled-angular-scanning surface plasmon resonance is smaller at a longer wavelength. Also, it is clear that the small incident angle is preferable to keep the half-angle small. For a given combination of a metal and dielectric material and when two values out of the following three values, wavelength of the exterior light, the resonance angle and the grating spacing, are given, the rest is calculated using eq (6).

Figure 7:
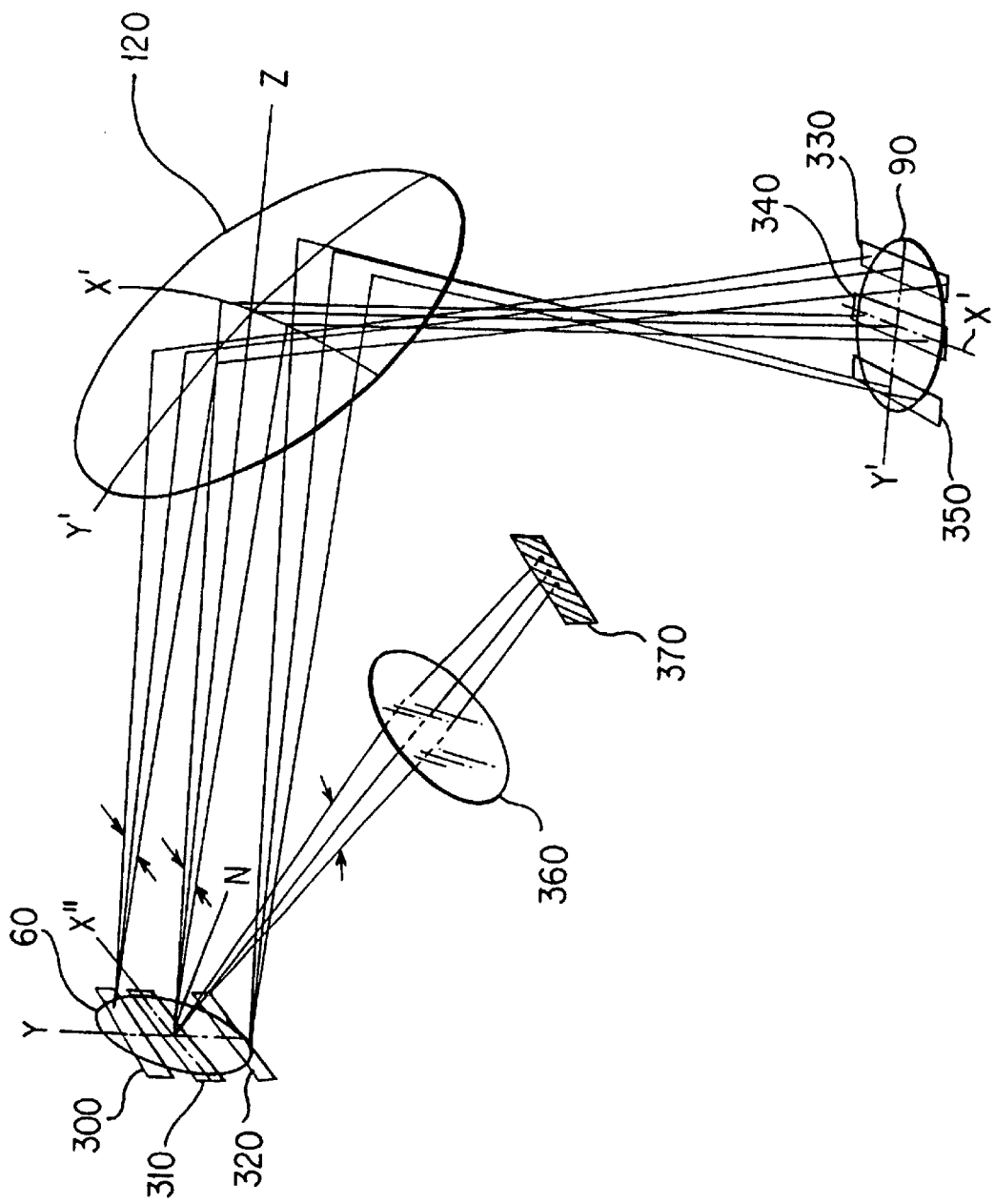
FIG. 7 and 8 show an additional embodiments of the invention using anamorphic imaging.

The full-angle widths as shown in FIG. 10 were calculated for a 400 to 100 nm wavelength range in the case of Gold-$H_2O$ combination and the grating constant of 1580 lines/mm. As shown in FIG. 7, the full-angle width is smaller at a longer wavelength. In addition, the width becomes abruptly large at a wavelength shorter than 700 nm. Thus, from the viewpoint of the surface plasmon resonance phenomenon, the wavelength should be longer than 700 nm.

Sampling Site Layout/isolation

Determining sample site configuration is dependent in part on the application. A transducer consisting of a single site is the simplest configuration, however, the most flexible configuration is the array. This is where the transducer is divided up into n×n sites. Each site capable of binding a unique molecule or acting as a control. The advantage of this configuration is the large number of sites that can be produced. For example an array 100×100 site gives you 10,000 possible interactive sites in a 1 cm sq. area. Each site provides for different types of chemistries. For example: 1. Compounds that recognize the same molecule but in a different mode (site) can be used to assign higher confidence to the detection method. 2. Different lots of the same compound can be used to assure quality of the chip. 3. Some of the site can be used a control sites for chemistry as well as hardware. This type of microscale controls can eliminate more expensive engineering and production steps by being able to eliminate artifacts due to things like transducer warpage, uneven sample introduction temperature control and etc. Linear arrays can also be used but their usefulness as compared to 2D arrays is limited. To help separate the sensor sites on the transducer from other adjacent sensor sites dikes may be used. Dikes are defined as fine line of material that encircles the active sites. These materials could vary depending on the function. For example a high photo adsorbent material could be used to prevent the resonance from propagating into adjacent sites. These dike material could also have hydrophobic properties to facilitate laying down the active surface (prevent run over to adjacent sites).

Site Size Considerations

For 1-D site array methods, the individual samples are ideally deposited on the SPRG in the shape of a bar, although other shapes can be used. The bars of the various individual samples are parallel to each other and separated by a distance approximately equal to their widths. Their centers can be connected with a line that is perpendicular to the long axis of the bars. This line is parallel to the SPR grating lines. The excited plasmon travels perpendicular to the grating lines and thus parallel to the length of the bar. For 2-D site array methods the samples are arranged on the SPRG in the shape of a rectangular grid. In the direction perpendicular to the grating lines, the length of the samples and their separations must be large enough to accommodate plasmon travel.

Design Considerations

Sample Density:
- trade-off between S/N and number of samples. The amount of light collected from each sample will be proportional to its area. The S/N will thus increase with sample area. The number of samples that can be placed on the SPRG will decrease with sample area.
- blurring of the image on the detector is another potential limiting factor of sample density.
- the sample length in the perpendicular direction must be as long as the plasmon travel.
- the ultimate limitation on sample density is the set by the minimum area which can be reliably placed on the SPRG.

Number of Samples:
- a trade off between number of samples and detector cost. The number of pixels that the detector must have will be proportional to the number of samples.
- the more samples, the larger the SPRG and the larger the optics.

For 1-D detector and site array systems, there is also a trade-off between S/N and detector height. The signal from each sample will be proportional to the length of the sample bars. However, the height of the array must also be increased in proportion to the length of the sample bars, thus increasing its cost.

What is claimed is:

1. An optical resonance analysis system comprising:
   illumination means for generating illumination of fixed multiple wavelengths further comprising:
      an array of elements each generating a different fixed wavelength; and
      an optical system which projects said illumination of fixed wavelengths;
   sensor means on which said illumination impinges which reflects or transmits said illumination; and,
   detection means for detecting said reflected or transmitted illumination.

2. The optical resonance analysis system of claim 1 wherein said sensor means further comprises a surface plasmon resonance device.

3. The optical resonance analysis system of claim 1 wherein said sensor means further comprises a waveguide device.

4. The optical resonance analysis system of claim 1 wherein said sensor means further comprises a multi-layered waveguide device.

5. The optical resonance analysis system of claim 1 wherein said sensor means is arranged as a one dimensional array of analysis sites.

6. The optical resonance analysis system of claim 1 wherein said sensor means is arranged as a two dimensional array of analysis sites.

7. The optical resonance analysis system of claim 1 wherein said detector means further comprises a charge coupled device camera.

8. The optical resonance analysis system of claim 1 wherein said detector means further comprises a charge injection device camera.

9. The optical resonance analysis system of claim 1 wherein said detector means further comprises an angle stop.

10. The optical resonance analysis system of claim 1 wherein said detector means further comprises a wavelength stop.

11. The optical resonance analysis system of claim 1 wherein said detector means further comprises an imaging lens.

12. The optical resonance analysis system of claim 1 wherein said detector means further comprises a polarizer.

13. An optical resonance analysis system comprising:
    illumination means for generating illumination of varying angles further comprising:
       a source comprised of an array of elements for generating illumination at a plurally of fixed angles; and
       a lens system for projecting said illumination at said plurality of fixed angles;
    sensor means on which said illumination impinges which reflects or transmits said illumination; and,
    detection means for detecting said reflected or transmitted illumination.

14. The optical resonance analysis system of claim 13 wherein said sensor means further comprises a surface plasmon resonance device.

15. The optical resonance analysis system of claim 13 wherein said sensor means further comprises a waveguide device.

16. The optical resonance analysis system of claim 13 wherein said sensor means further comprises a multi-layered waveguide device.

17. The optical resonance analysis system of claim 13 wherein said sensor means is arranged as a one dimensional array of analysis sites.

18. The optical resonance analysis system of claim 13 wherein said sensor means is arranged as a two dimensional array of analysis sites.

19. The optical resonance analysis system of claim 13 wherein said detector means further comprises a charge coupled device camera.

20. The optical resonance analysis system of claim 13 wherein said detector means further comprises a charge injection device camera.

21. The optical resonance analysis system of claim 13 wherein said detector means further comprises an angle stop.

22. The optical resonance analysis system of claim 13 wherein said detector means further comprises a wavelength stop.

23. The optical resonance analysis system of claim 13 wherein said detector means further comprises an imaging lens.

24. The optical resonance analysis system of claim 13 wherein said detector means further comprises a polarizer.

25. An optical resonance analysis system comprising:
    sensor means;
    illumination means for generating non-monochromatic illumination having a plurality of wavelengths further comprising:
       means for generating illumination at a plurality of angles;
       a lens system for projecting said illumination at said plurality of angles; and
       a dispersive device for dispersing said illumination at each of said plurality of angles so that there is a correlation between said plurality of angles and the wavelengths of said illumination such that a resonance condition is generated on said sensor means for all wavelengths generated by said non-monochromatic source simultaneously;
    detection means for detecting said reflected or transmitted illumination.

26. The optical resonance analysis system of claim 25 wherein said sensor means further comprises a surface plasmon resonance device.

27. The optical resonance analysis system of claim 25 wherein said sensor means further comprises a waveguide device.

28. The optical resonance analysis system of claim 25 wherein said sensor means further comprises a multi-layered waveguide device.

29. The optical resonance analysis system of claim 25 wherein said sensor means is arranged as a one dimensional array of analysis sites.

30. The optical resonance analysis system of claim 25 wherein said sensor means is arranged as a two dimensional array of analysis sites.

31. The optical resonance analysis system of claim 25 wherein said detector means further comprises a charge coupled device camera.

32. The optical resonance analysis system of claim 25 wherein said detector means further comprises a charge injection device camera.

33. The optical resonance analysis system of claim 25 wherein said detector means further comprises an angle stop.

34. The optical resonance analysis system of claim 25 wherein said detector means further comprises a wavelength stop.

35. The optical resonance analysis system of claim 25 wherein said detector means further comprises an imaging lens.

36. The optical resonance analysis system of claim 25 wherein said detector means further comprises a polarizer.

37. An optical resonance analysis system comprising:
   illumination means for generating illumination further comprising:
      a source; and
      positioning means for independently positioning said source rotationally and axially;
   sensor means on which said illumination impinges which reflects or transmits said illumination; and,
   detection means for detecting said reflected or transmitted illumination.

38. The optical resonance analysis system of claim 37 wherein said sensor means further comprises a surface plasmon resonance device.

39. The optical resonance analysis system of claim 37 wherein said sensor means further comprises a waveguide device.

40. The optical resonance analysis system of claim 37 wherein said sensor means further comprises a multi-layered waveguide device.

41. The optical resonance analysis system of claim 37 wherein said sensor means is arranged as a one dimensional array of analysis sites.

42. The optical resonance analysis system of claim 37 wherein said sensor means is arranged as a two dimensional array of analysis sites.

43. The optical resonance analysis system of claim 37 wherein said detector means further comprises a charge coupled device camera.

44. The optical resonance analysis system of claim 37 wherein said detector means further comprises a charge injection device camera.

45. The optical resonance analysis system of claim 37 wherein said detector means further comprises an angle stop.

46. The optical resonance analysis system of claim 37 wherein said detector means further comprises a wavelength stop.

47. The optical resonance analysis system of claim 37 wherein said detector means further comprises an imaging lens.

48. The optical resonance analysis system of claim 37 wherein said detector means further comprises a polarizer.

49. The optical resonance analysis system of claim 37 wherein said positioning means further comprises:
   a housing;
   rotation means for rotating said source
   a cylinder having pseudo-helical slots; and
   pins extending from said rotation means to engage said pseudo-helical slots.

50. Positioning means for independently positioning an item rotationally and axially comprising:
   a housing;
   rotation means for rotating said item;
   a cylinder having pseudo-helical slots; and
   pins extending from said rotation means to engage said pseudo-helical slots.

51. An optical resonance analysis system comprising:
   illumination means for generating illumination;
   anamorphic imaging means
   sensor means on which said illumination impinges which reflects or transmits said illumination; and,
   detection means for detecting said reflected or transmitted illumination.

52. The optical resonance analysis system of claim 51 wherein said sensor means further comprises a surface plasmon resonance device.

53. The optical resonance analysis system of claim 51 wherein said sensor means further comprises a waveguide device.

54. The optical resonance analysis system of claim 51 wherein said sensor means further comprises a multi-layered waveguide device.

55. The optical resonance analysis system of claim 51 wherein said sensor means is arranged as a one dimensional array of analysis sites.

56. The optical resonance analysis system of claim 51 wherein said sensor means is arranged as a two dimensional array of analysis sites.

57. The optical resonance analysis system of claim 51 wherein said sensor means is comprises a charge coupled device camera.

58. The optical resonance analysis system of claim 51 wherein said sensor means is comprises a charge injection device camera.

59. The optical resonance analysis system of claim 51 wherein said sensor means is comprises an angle stop.

60. The optical resonance analysis system of claim 51 wherein said sensor means is comprises a wavelength stop.

61. The optical resonance analysis system of claim 51 wherein said sensor means is comprises an imaging lens.

62. The optical resonance analysis system of claim 51 wherein said sensor means is comprises a polarizer.

63. An optical resonance analysis system comprising:
   an illumination source for generating illumination, said source comprising a dispersive device which disperses said illumination;
   a sensor which reflects or transmits said illumination from said illumination source;
   an anamorphic optical system which images said illumination from said sensor; and
   a detector which detects said illumination from said anamorphic optical system.

64. The optical resonance analysis system of claim 63 wherein said sensor further comprises a surface plasmon resonance device.

65. The optical resonance analysis system of claim 63 wherein said sensor further comprises a waveguide device.

* * * * *

UNITED STATES PATENT AND TRADEMARK OFFICE
CERTIFICATE OF CORRECTION

PATENT NO.   : 6,600,563 B1
DATED        : July 29, 2003
INVENTOR(S)  : Dar Bahatt et al.

It is certified that error appears in the above-identified patent and that said Letters Patent is hereby corrected as shown below:

<u>Column 13,</u>
Line 64, "derivatised/sensitized???" should read -- derivatised/sensitized --.

<u>Column 15,</u>
Line 21, "the polarizer (???)" should read -- the polarizer --.

Signed and Sealed this

Seventh Day of October, 2003

JAMES E. ROGAN
*Director of the United States Patent and Trademark Office*